United States Patent
Chu

(10) Patent No.: US 8,920,306 B2
(45) Date of Patent: Dec. 30, 2014

(54) DEVICES AND METHODS FOR DELIVERING A PELVIC IMPLANT

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1244 days.

(21) Appl. No.: 12/341,399

(22) Filed: Dec. 22, 2008

(65) Prior Publication Data

US 2009/0171139 A1 Jul. 2, 2009

Related U.S. Application Data

(60) Provisional application No. 61/017,211, filed on Dec. 28, 2007.

(51) Int. Cl.
*A61F 2/00* (2006.01)
*A61B 17/06* (2006.01)
*A61B 17/221* (2006.01)
*A61B 17/22* (2006.01)
*A61B 17/00* (2006.01)

(52) U.S. Cl.
CPC ..... *A61F 2/0045* (2013.01); *A61B 2017/06019* (2013.01); *A61B 17/221* (2013.01); *A61B 17/06109* (2013.01); *A61B 17/06004* (2013.01); *A61B 2017/22035* (2013.01); *A61B 17/06066* (2013.01); *A61B 2017/06095* (2013.01); *A61B 2017/06052* (2013.01); *A61B 2017/2212* (2013.01); *A61B 2017/00805* (2013.01)
USPC ............................................... 600/37; 600/29

(58) Field of Classification Search
CPC ........... A61B 2017/00809; A61B 2017/00805; A61B 17/06109; A61B 17/221; A61B 2017/06052; A61B 2017/22035; A61B 2017/2212
USPC .......... 600/29, 30, 37; 128/897, 899; 606/151, 606/110, 113, 139, 148
See application file for complete search history.

(56) References Cited

U.S. PATENT DOCUMENTS 4,935,027 A 6/1990 Yoon
5,108,406 A 4/1992 Lee
(Continued)

FOREIGN PATENT DOCUMENTS

EP 1 201 189 A2 5/2002
EP 1 508 305 A2 2/2005
(Continued)

OTHER PUBLICATIONS

International Search Report and Written Opinion for International Application No. PCT/US08/88103, mailed on Aug. 17, 2009; 15 pages.

(Continued)

*Primary Examiner* — Charles A Marmor, II
*Assistant Examiner* — Shannon McBride

(57) ABSTRACT

An apparatus according to an embodiment of the invention includes an elongate body having a distal end configured to releasably couple the elongate body to a delivery device. A lock tube is movably disposable within a lumen of the elongate body. A connector is disposed at a proximal end of the elongate body and is configured to releasably couple a pelvic implant to the elongate body. The lock tube is configured to be slidably moved to a position adjacent the pelvic implant to secure the pelvic implant to the elongate body. A method according to an embodiment of the invention includes placing a portion of an implant through an opening defined by a dilator. A first elongate body of the dilator is moved relative to a second elongate body of the dilator to secure the implant to the dilator.

14 Claims, 20 Drawing Sheets

(56) References Cited

U.S. PATENT DOCUMENTS

| | | | |
|---|---|---|---|
| 5,330,491 A * | 7/1994 | Walker et al. | 606/148 |
| 5,403,331 A * | 4/1995 | Chesterfield et al. | 606/148 |
| 5,562,678 A | 10/1996 | Booker | |
| 5,571,120 A * | 11/1996 | Yoon | 606/148 |
| 5,741,277 A | 4/1998 | Gordon et al. | |
| 5,899,909 A | 5/1999 | Claren et al. | |
| 6,077,250 A * | 6/2000 | Snow et al. | 604/174 |
| 6,273,852 B1 | 8/2001 | Lehe et al. | |
| 6,478,727 B2 | 11/2002 | Scetbon | |
| 6,491,703 B1 | 12/2002 | Ulmsten | |
| 6,524,328 B2 * | 2/2003 | Levinson | 606/232 |
| 6,612,977 B2 | 9/2003 | Staskin et al. | |
| 6,638,209 B2 | 10/2003 | Landgrebe | |
| 6,638,210 B2 | 10/2003 | Berger | |
| 6,641,525 B2 | 11/2003 | Rocheleau et al. | |
| 6,652,450 B2 | 11/2003 | Neisz et al. | |
| 6,908,425 B2 | 6/2005 | Luscombe | |
| 6,911,003 B2 | 6/2005 | Anderson et al. | |
| 7,048,682 B2 | 5/2006 | Neisz et al. | |
| 7,083,568 B2 | 8/2006 | Neisz et al. | |
| 7,083,637 B1 | 8/2006 | Tannhauser | |
| 7,090,686 B2 | 8/2006 | Nobles et al. | |
| 7,112,171 B2 | 9/2006 | Rocheleau et al. | |
| 7,122,039 B2 | 10/2006 | Chu | |
| 7,131,943 B2 | 11/2006 | Kammerer | |
| 7,131,944 B2 | 11/2006 | Jacquetin | |
| 7,223,229 B2 | 5/2007 | Inman et al. | |
| 7,229,404 B2 * | 6/2007 | Bouffier | 600/30 |
| 7,351,197 B2 | 4/2008 | Montpetit et al. | |
| 8,057,511 B2 * | 11/2011 | Flores et al. | 606/232 |
| 2003/0109874 A1 * | 6/2003 | Dennis | 606/47 |
| 2004/0181243 A1 | 9/2004 | Chu et al. | |
| 2004/0225181 A1 | 11/2004 | Chu et al. | |
| 2005/0038452 A1 | 2/2005 | Chu | |
| 2005/0075660 A1 | 4/2005 | Chu et al. | |
| 2005/0107660 A1 | 5/2005 | Valtchev | |
| 2005/0131391 A1 | 6/2005 | Chu et al. | |
| 2005/0177022 A1 | 8/2005 | Chu et al. | |
| 2005/0277807 A1 | 12/2005 | MacLean et al. | |
| 2006/0058575 A1 | 3/2006 | Zaddem et al. | |
| 2006/0089524 A1 | 4/2006 | Chu | |
| 2006/0089525 A1 | 4/2006 | Mamo et al. | |
| 2006/0173468 A1 * | 8/2006 | Simmon et al. | 606/113 |
| 2007/0123746 A1 * | 5/2007 | MacLean | 600/30 |
| 2008/0045782 A1 * | 2/2008 | Jimenez | 600/30 |

FOREIGN PATENT DOCUMENTS

| | | |
|---|---|---|
| WO | WO 2005/122721 A2 | 12/2005 |
| WO | WO 2006/046950 A1 | 5/2006 |
| WO | WO 2007/016698 A2 | 2/2007 |
| WO | WO 2007/019274 A2 | 2/2007 |
| WO | WO 2007/019374 A2 | 2/2007 |
| WO | WO 2007/059199 A2 | 5/2007 |

OTHER PUBLICATIONS

International Preliminary Report on Patentability for PCT Application No. PCT/US2008/088103, mailed on Jul. 8, 2010, 11 pages.

Communication Relating To The Results of the Partial International Search for PCT/US08/88103, mailed on May 13, 2009; 2 pages.

* cited by examiner

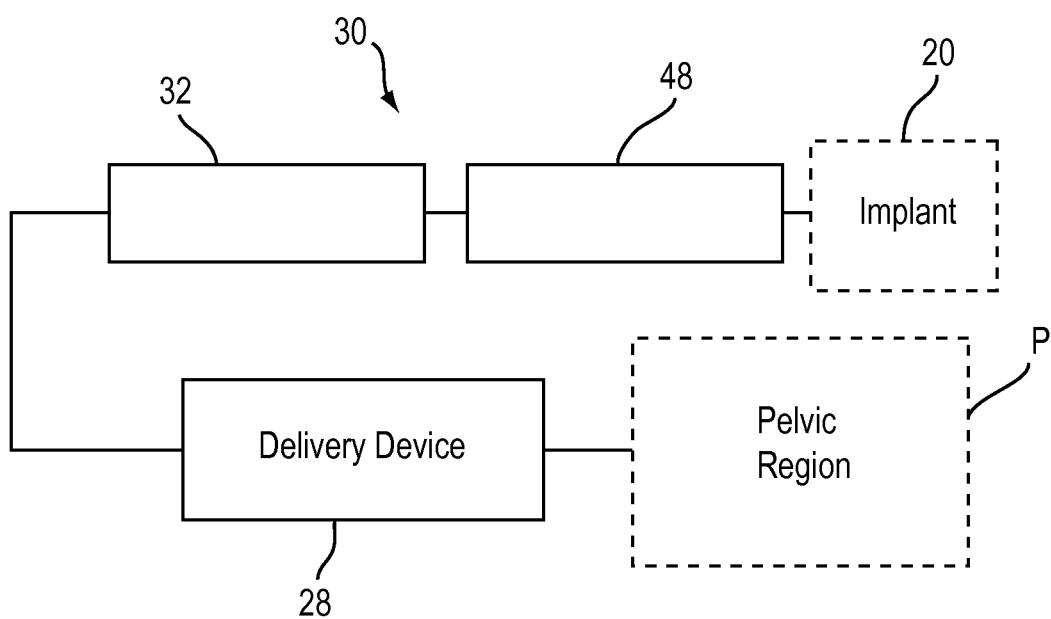

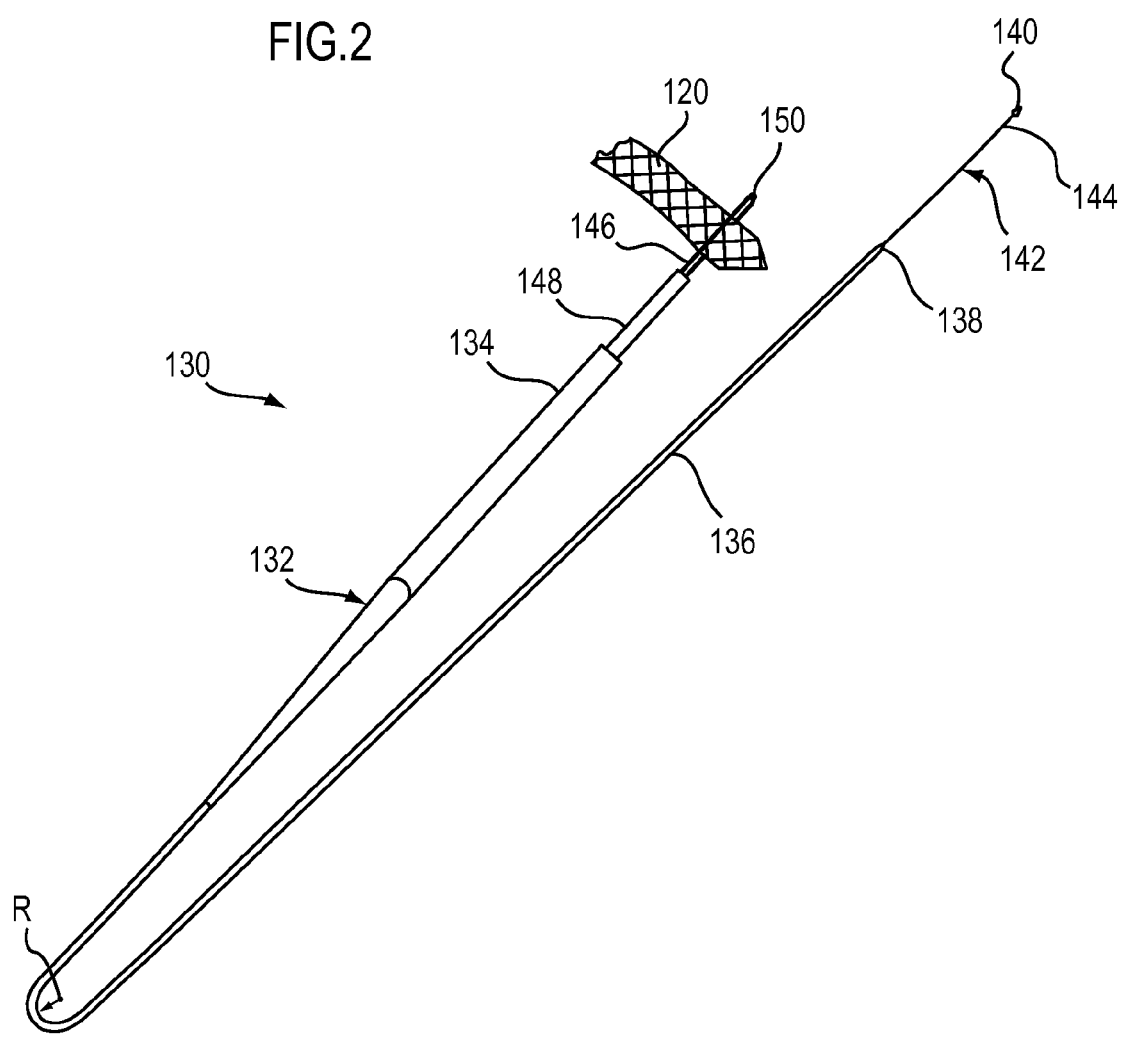

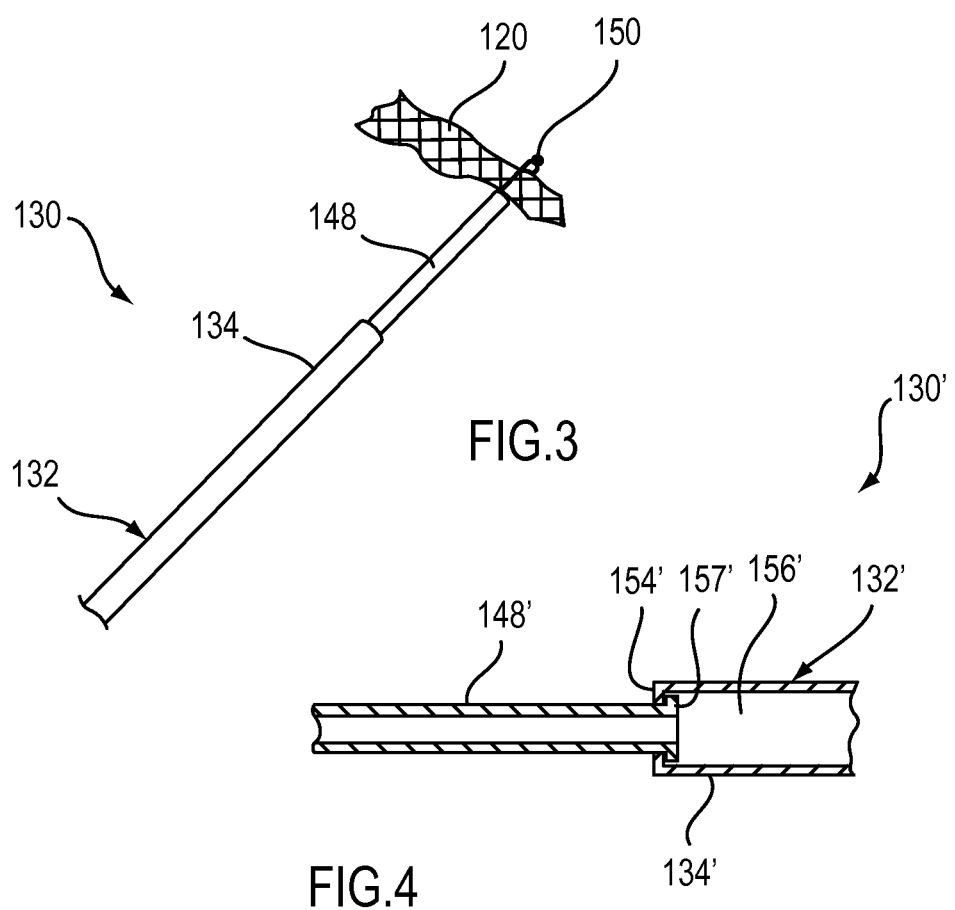

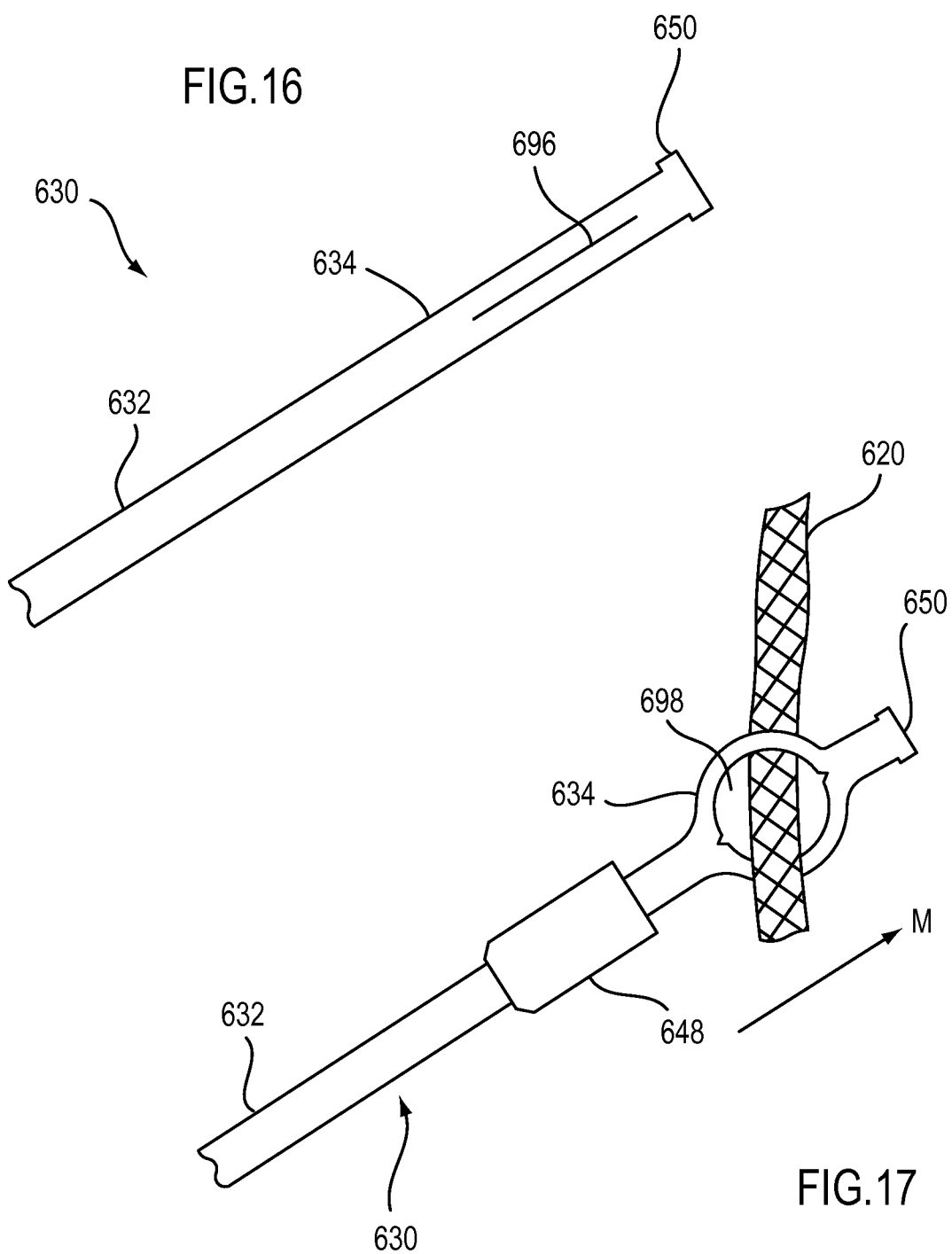

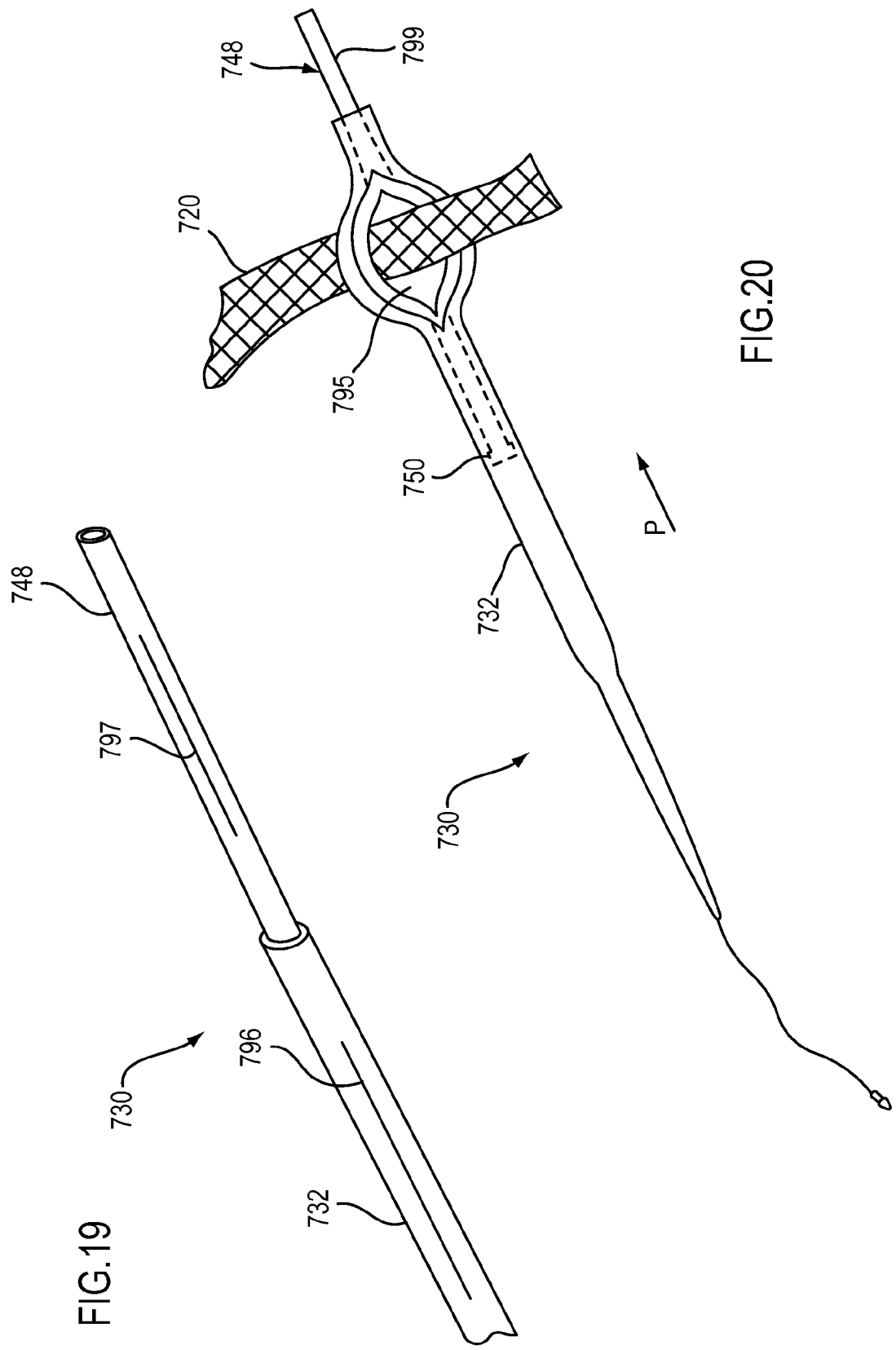

DEVICES AND METHODS FOR DELIVERING A PELVIC IMPLANT

CROSS-REFERENCE TO RELATED APPLICATIONS

This application claims priority to U.S. Provisional Patent Application Ser. No. 61/017,211, entitled "Devices and Methods for Delivering a Pelvic Implant," filed Dec. 28, 2007, the disclosure of which is hereby incorporated by reference in its entirety.

BACKGROUND

The disclosed invention relates generally to medical devices and more particularly to devices and methods for delivering an implant within a pelvic region to treat various female pelvic dysfunctions.

A variety of medical procedures are performed to treat various female pelvic dysfunctions, including procedures to treat urinary incontinence, and correcting various conditions uterine prolapse, cystoceles, rectoceles, and vaginal vault prolapse.

A vaginal prolapse can be caused due to age or other factors and typically results in one of three types of prolapse: hysterocele, cystocele, and rectocele. A hysterocele occurs when the uterus descends into the vagina and is often treated with a hysterectomy followed by a vaginal vault suspension. A cystocele occurs when the bladder bulges or descends into the vagina, and a rectocele occurs when the rectum bulges or descends into the vagina. It is often common for multiple prolapses to occur at the same time. Treatment of vaginal prolapse can include a suturing procedure or the use of an implant for support or suspension.

Various devices and procedures are used to deliver and secure such pelvic implants within a variety of different anatomical structures within a pelvic region. Implants can be delivered to a pelvic region through a single vaginal incision, and/or through exterior incisions in the patient. Various complications can occur due to, for example, space constraints for performing an implantation procedure. Often, implants can become damaged during delivery due to the type of delivery device and/or the type of implant, or due to excessive handling of the implant during the implant procedure. Thus, it is desirable to improve the delivery process associated with a pelvic implant to help prevent damage to the implant during implantation.

Thus, a need exists for devices and methods for delivering pelvic implants to treat various pelvic dysfunctions that provide improved coordination and organization of the placement of an implant and/or reduce damage to the implant during delivery.

SUMMARY OF THE INVENTION

An apparatus according to an embodiment of the invention includes an elongate body having a distal end configured to releasably couple the elongate body to a delivery device. A lock tube is movably disposable within a lumen of the elongate body. A connector disposed at a proximal end of the elongate body and is configured to releasably couple a pelvic implant to the elongate body. The lock tube is configured to be slidably moved to a position adjacent the pelvic implant to secure the pelvic implant to the elongate body. A method according to an embodiment of the invention includes placing a portion of an implant through an opening defined by a dilator. A first elongate body of the dilator is moved relative to a second elongate body of the dilator to secure the implant to the dilator.

BRIEF DESCRIPTION OF THE DRAWINGS

FIG. 1 is a schematic illustration of various devices and a pelvic region.

FIG. 2 is a top view of an embodiment of a dilator device shown in a first configuration and a portion of an embodiment of an implant.

FIG. 3 is a top view of a proximal end portion of the dilator device of FIG. 2 shown in a second configuration.

FIG. 4 is a side cross-sectional view of a portion of another embodiment of a dilator device.

FIG. 16 is a side perspective view of an elongate body of another embodiment of a dilator device shown in a closed configuration.

FIG. 17 is a side perspective view of a portion of the dilator device of FIG. 16 shown with the elongate body in an open configuration, a lock tube in a first position, and an embodiment of an implant.

FIG. 19 is a side perspective view of a portion of an embodiment of a dilator device shown in a closed configuration.

FIG. 20 is a side perspective view of the portion of dilator device of FIG. 19 shown in an open configuration and a portion of an embodiment of an implant.

DETAILED DESCRIPTION

Figure 5:
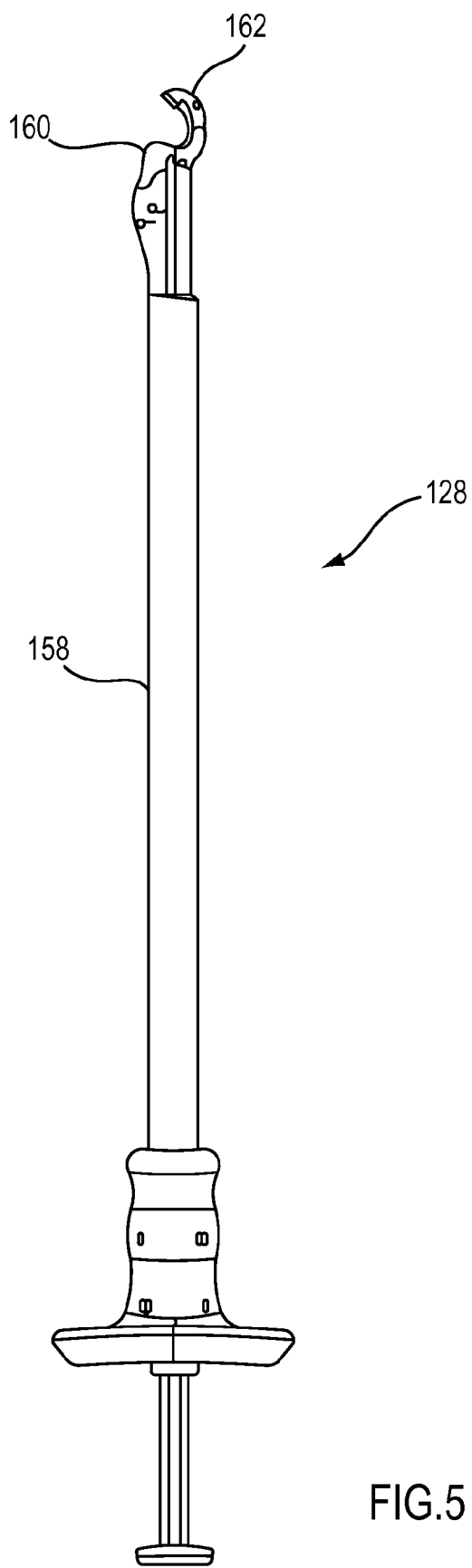
FIG. 5 is a side view of an embodiment of a delivery device.

The devices and methods described herein are generally directed to the delivery and placement of an implant (e.g., a urethral sling or a uterine support device) to an anatomical site within a patient. For example, the devices and methods are suitable for delivering an implant to a pelvic region of a patient. An implant can be placed into the pelvic space of a patient and secured at one or more locations within the pelvic space to treat many different female pelvic floor dysfunctions, such as, for example, cystoceles, rectoceles and enteroceles. An implant can be secured to various tissue portions, such as, for example, a sacrospinous ligament, a ureterosacral ligament, a pubo-urethral tissue, obturator fossa, an arcus tendineus, an obturator muscle, a levator ani muscle or any levator muscle, or any other selected tissue site within the pelvic region. A single implant or multiple implants can be used in a single procedure. In some applications, when multiple implants are used, support can be provided in desired areas and improved control of the direction of stretch or support of the implant can be achieved. Various dilator devices and delivery devices are also described for delivering and securing an implant within a pelvic region of a patient.

Various dilator devices are described herein that can be used in conjunction with a delivery device to deliver and place an implant to a desired location within a pelvic region. For example, a portion of an implant, such as a strap or arm, can be associated to a dilator device and the dilator device can be coupled to a delivery device. With an implant coupled to the dilator device, the dilator device can be passed through a tissue site using the delivery device. Because the implant is coupled to the dilator device, as the dilator device is moved through tissue, the implant will follow the path of the dilator. A portion of the implant can then remain within the tissue for anchoring.

In some embodiments, an implant can be associated to a dilator device after the dilator has been placed within a pelvic region. For example, in an embodiment of an implant having multiple straps, such as with a pelvic floor repair implant, prior placement of the dilator can help with coordinating and organizing the placement of the various straps. Placing the dilator(s) within a pelvic region first also helps reduce handling of the implant during the implantation procedure, which can reduce damage to the implant. In some embodiments, multiple dilator devices are used to deliver and place an implant. For example, an implant can have multiple straps or arms, each configured to be secured to a different tissue portion within a pelvic region. A separate dilator can be used to deliver each arm or strap of the implant. The separate dilators can have the dame configuration or a different configuration. In some embodiments, a single dilator is used to sequentially place multiple straps or arms of an implant within a pelvic region.

In some embodiments, a dilator device can be used to lead an implant or a strap of an implant through a tissue in an intracorporeal location (i.e., within a patient's body) such as the sacrospinous ligament or arcus tendineus. In other embodiments, a dilator can be used to lead an implant or a strap of an implant through a tissue and to an extracorporeal location (i.e., outside of a patient's body) such as through an obturator membrane or behind a pubic bone and then out through an exterior incision in the patient's body.

An apparatus according to an embodiment of the invention includes an elongate body having a distal end configured to releasably couple the elongate body to a delivery device. A lock tube is movably disposed within a lumen of the elongate body. A connector is disposed at a proximal end of the elongate body, the connector is configured to releasably couple a pelvic implant to the elongate body. The lock tube is configured to be slidably moved to a position adjacent the pelvic implant to secure the pelvic implant to the elongate body.

An apparatus according to another embodiment of the invention includes an elongate body movable between an expanded configuration and a collapsed configuration. The elongate body in the expanded configuration defines an opening at a proximal end portion configured to receive therethrough a portion of a pelvic implant. A lock member is slidably disposed over at least a portion of the elongate body. The lock member is configured to move between a first position in which the elongate body is in the expanded configuration and a second position in which the elongate body is in the collapsed configuration and the lock member is disposed at least partially over the opening of the elongate body.

An apparatus according to another embodiment includes a first elongate body having an expanded configuration and a collapsed configuration and a second elongate body having an expanded configuration and a collapsed configuration. The second elongate body is at least partially disposed within a lumen of the first elongate body. The first elongate body in its expanded configuration defines an opening on a proximal end portion of the first elongate body. The second elongate body in the expanded configuration defines an opening on a proximal end portion of the second elongate body. The second elongate body when in the expanded configuration is configured to receive at least a portion of an implant through the opening of the second elongate body. The second elongate body in the collapsed configuration is configured to secure the pelvic implant to the apparatus.

An implant according to an embodiment of the invention can include a tanged portion and a detanged portion. The terms "tanged" or "tangs" as used herein mean roughened or jagged edges or areas, such as can result from cutting a woven or knit mesh material. The tanged portion can be used, for example, to anchor or secure the implant to tissue. An implant according to an embodiment of the invention can be implanted, for example, through a vaginal incision, and placed bilaterally in a direction toward an obturator muscle, in a retro-pubic direction (behind the pubic bone), or in a pre-pubic direction (in front of the pubic bone). In other embodiments, an implant can be placed in the direction of other anatomical structures as desired. Although a single vaginal incision procedure for treating female pelvic floor dysfunctions is described herein, other procedures can be performed using the devices and methods described herein.

As used herein, the term proximal refers to the portion or end of a device that is closest to a physician when performing a medical procedure, and the term distal refers to the portion or end of the device that is furthest from the physician during a medical procedure. For example, a distal end or portion of a dilator device as described herein refers to the end or portion of the dilator device that is first inserted into a body of a patient during a medical procedure. The proximal end or portion is the end or portion of the dilator that is inserted into a body of the patient after the distal end or portion.

FIG. 1 is a schematic illustration of various devices and a schematic representation of a pelvic region of a patient. An implant 20 (also referred to herein as implant member or pelvic implant) can be any of a variety of different types of pelvic implants used to treat various female pelvic dysfunctions. For example, the implant 20 can be a urethral sling, an implant configured to support a uterus, or a total pelvic repair implant. One or more implants 20 can be implanted within a variety of different locations within a pelvic region of a patient. The implant 20 can be delivered through a single incision within a vagina of a patient and thereafter secured and/or deposited within pelvic tissue. Portions of an implant can also be secured through an exterior incision of a patient.

Pelvic tissue can include, for example, ligaments, muscle, fascia, or any other structure or soft tissue within a pelvic region of a patient.

The implant 20 can be formed with a mesh material to allow tissue in-growth to the implant 20 after implantation. For example, the implant 20 can be formed with a mesh material as described in U.S. Patent Pub. 2005/0038452 A1 to Chu, the disclosure of which is hereby incorporated by reference in its entirety. In some embodiments, the entire implant 20 can be formed with a mesh material, whereas in other embodiments, only a portion of the implant 20 is formed with a mesh material. The implant 20 can be monolithically formed. Alternatively, the implant 20 can be formed with multiple different materials and/or can include multiple different components or portions coupled together.

The implant 20 can include an elongate body portion, such as used to support a urethra to treat urinary incontinence. An implant 20 can include one or more straps or arms extending from the body portion that can be secured to various tissue portions within a pelvic region. The implant 20 can include a tanged edge or tanged portion to secure a strap or other portion of the implant 20 to a tissue portion, T1 or T2 within a pelvic region P (schematically illustrated in FIG. 1). As stated above, the tangs allow the implant 20 to be anchored within pelvic tissue without the use of additional anchoring mechanisms or sutures. In some embodiments, an implant includes tangs on an edge along an entire length of the implant 20. In other embodiments, the implant 20 includes tangs covering substantially all of an exterior surface of the implant. In some embodiments, tangs are only on the straps or arms of the implant 20.

An implant 20 can be a variety of different shapes, sizes and configurations depending on the particular need and/or medical treatment. For example, the implant 20 can be substantially rectangular, square, oval, or elliptical. The implant 20 can be formed with various widths, lengths and thicknesses and the implant 20 can be uniformly formed (e.g., the same thickness and/or width) along the length of the implant 20. Alternatively, the dimensions of the implant 20, can vary along its length. For example, the straps of the implant 20 can be tapered.

An implant 20 can be coupled to various tissues within the pelvic region P, such as, for example, a levator muscle (e.g., levator ani muscle), a sacrospinous ligament, a tendineus arch of levator muscle (also referred to herein as "arcus tendineus" or "white line"), or to an iliococcygeus muscle, or to other anatomical securement sites within the pelvic region of a patient. For example, straps of the implant 20 can be deposited at selected tissue sites T1 and T2 within the pelvic region P, such that the support portion of the implant 20 is positioned beneath a urethra R or a uterus U of the patient. In some embodiments, the implant 20 can be used to support a uterus U of the patient. The implant 20 can also be coupled to a vagina V of the patient, such as to the vaginal apex, to a wall of the vagina V, secured inside the vagina (e.g., within a vaginal lumen) or within the pelvic region. In some embodiments, only one implant is implanted on one side of the pelvic region P. In other embodiments, more than one implant 20 is implanted. For example, a first implant can be secured on one side of a pelvic region of a patient, and a second implant can be secured on a contra lateral side of the pelvic region. In yet other embodiments, the implant is sized to extend from one side of the pelvic region to the other side of the pelvic region, or to span a substantial portion of the pelvic floor such as in total pelvic floor repairs.

The implant 20 can be delivered into the pelvic region P using a delivery device 28 together with one or more dilator devices 30. The delivery device 28 can be, for example, a Capio® Suture Capture Device or an Obtryx® Halo device, each of which are manufactured by Boston Scientific Corporation. Other types of devices can alternatively be used, such as, for example, the suturing device described in U.S. Patent Pub. 2004/0181243 A1 to Chu et al., entitled Re-shapeable Medical Device, the disclosure of which is hereby incorporated by reference in its entirety. The pelvic tissues T1 and T2 can be, for example, a levator an muscle, a sacrospinous ligament, a tendineus arch of levator muscle, an iliococcygeus muscle or other anatomical structure or tissue within a pelvis. The delivery device 28 can also be used to pass a suture end through a wall of a vagina or to pass a suture through the epithelium of a vaginal wall without passing the suture through the vaginal wall.

The dilator device 30 (also referred to herein as dilator) includes an elongate body 32 that has a distal end configured to be associated to a delivery device 28 and a proximal end configured to releasably couple an implant 20 thereto. For example, the dilator 30 can include a suture at a distal end, and a trocar needle coupled to the suture. The trocar needle can be used to associate the dilator 30 to a delivery device 28, such as, for example, a Capio® device mentioned above. In other embodiments, the distal end of the dilator 30 includes a loop or other type of connector that can be used to associate the dilator 30 to a delivery device 28, such as, for example, a Halo device mentioned above.

The dilator 30 can also include a connector 48 on the proximal end to couple an implant 20 to the dilator 30. The connector 48 can be a variety of different configurations and can include, for example, a loop connector, one or more lock tubes, expandable and collapsible members, or other connectors described in more detail herein. The dilator 30 can also be color-coded. For example, when an implant having multiple arms or straps is to be delivered to a pelvic region, a separate dilator having a unique color can be associated to each strap of the implant. Such color-coding can help with the organization of the delivery process.

The dilator 30, together with the delivery device 28, can be used to insert and deposit the implant 20 within a pelvic region of a patient. The dilator 30 can be coupled to the implant 20 prior to the dilator 30 being placed within a pelvic region of a patient, or after the dilator 30 has been placed. For example, if the implant 20 includes multiple straps or arms such as with a pelvic floor repair implant, the implant can be associated to the dilator 30 after the dilator 30 has been placed within the pelvic region using a delivery device 28. Placing the dilator 30 into the patient's body prior to attaching the implant to the dilator 30, minimizes handling of the implant and can thus help reduce damage to the implant during delivery. In addition, inserting the dilator 30 into the pelvic region without the implant attached can improve visibility during positioning of the dilator 30.

With the implant 20 coupled to the dilator 30, and the dilator 30 coupled to the delivery device 28, the delivery device 28 can be used to deliver the implant 20 into a pelvic region. Specifically, the dilator 30 can be inserted through a vaginal incision and into the pelvic region using a transvaginal approach using the delivery device 28. As stated above, there are various different types of delivery device 28. For example, some embodiments of a delivery device 28 have an articulating head, others have multiple carriers, while still others have a re-shapeable shaft. The particular embodiment of a delivery device used can depend on the particular problem being treated and the reachability of the attachment location within the pelvic region.

Having described above various general principles, several exemplary embodiments of these concepts are now described. These embodiments are only examples, and many other configurations of an implant 20, delivery device 28 and dilator device 30 are contemplated, and will be apparent to the artisan in view of the general principles described above and the exemplary embodiments.

FIGS. 2 and 3 illustrate a dilator device 130 (also referred to as "dilator") according to an embodiment of the invention with a portion (e.g., strap) of an implant 120 coupled thereto. The dilator 130 includes an elongate body 132 that defines a lumen (not shown). The elongate body 132 can be bent or curved to maneuver the dilator 130 within a pelvic region of a patient. The elongate body 138 can be formed with a material (e.g., a polymer) such that the dilator 130 is flexible and can make a turn, for example, of around 180 degrees when inserted into a patient's body. In FIG. 2, the elongate body 132 is shown turned approximately 180 degrees, with a radius of the turn R. The radius of the turn R can be, for example, 0.236 inches (6 mm). The elongate body 132 can be bent or curved to accommodate various degrees of turn and have a radius of turn R greater than or less than 6 mm. In some embodiments, the radius of the turn is substantially equal to a diameter of a carrier of a delivery device as described herein.

The elongate body 132 can be tapered, as shown in FIG. 2, such that the elongate body 132 has a greater outer diameter at a proximal end portion 134 than at a distal end portion 136. The distal end portion 136 includes a distal tip 138 that is coupled to a leader 142. The smaller diameter at the distal end portion 136 allows for easy transition from the leader 142 to the distal end portion 136 of the elongate body 132 when being inserted through tissue, which is described in more detail below. A trocar needle 140 is coupled to a distal end 144 of the leader 142. The trocar needle 140 can be releasably coupled to a delivery device, as described in more detail below.

The leader 142 can be formed with various materials including, for example, a polymer, metal or fibers. The leader 142 can be, for example, a suture. The leader 142 can be coupled to the elongate body 132 at multiple points along the length of the elongate body 132. The leader 142 can be coupled to the elongate body 132 with, for example, adhesives, thermal bonding, knotting, or other suitable coupling means. The leader 142 is disposed through the lumen (not shown) of the elongate body 132 and forms a loop 146 extending from the proximal end portion 134 of the elongate body 132. The loop 146 can be formed, for example, by knotting or crimping (not shown) the leader 142. As shown in FIG. 2, a portion of the implant 120 is placed through the loop 146. The distal end portion 144 of the leader 142 can vary in length. For example, a relatively short distal end portion 144 of the leader 142 can allow for a delivery device to pull a portion of the distal end portion 136 of the elongate body 132 into tissue as the delivery device is removed from the body. A relatively long distal end portion 144 of the leader 142 can allow for the removal of the trocar needle 140 from the delivery device external to a patient's body before the distal end portion 136 of the elongate body 132 is pulled through the tissue. In either case, a user can elect to grip the distal end portion 136 of the elongate body 132 to pull the dilator 130 through the tissue.

A lock tube 148 is coupled to the elongate body 132 and is partially disposed within the lumen of the elongate body 132. As shown in FIG. 3, the lock tube 148 can slide relative to the elongate body 132 to a position adjacent to or in contact with the implant 120 or a stop member 150 on the loop 146. The stop member 150 can be, for example, a knot formed in the leader 142. The stop member 150 prevents the lock tube 148 from sliding off the loop 146. In this embodiment, the lock tube 148 only moves to a position abutting the implant 120 to secure the portion of the implant 120 to the dilator 130.

In some embodiments, the lock tube 148 can be coupled to the elongate body 132 with a friction fit such that the lock tube 148 can be slidably moved relative to the elongate body 132, and can maintain a selected longitudinal position relative to the elongate body 132. In some embodiments, a lock tube can include a stop member as shown in the embodiment of FIG. 4. A portion of a dilator device 130' is shown in FIG. 4. The dilator device 130' includes a lock tube 148' that has a flange 157' that can contact a corresponding flange 154' of an elongate body 132'. The flanges 157' and 154' prevent the lock tube 148' from sliding completely out of a lumen 156' of the elongate body 132'.

Referring back to FIGS. 2 and 3, as stated above, the trocar needle 140 is used to associate the dilator device 130 to a delivery device. A delivery device 128 as illustrated in FIG. 5 can be, for example, a Capio® device mentioned above. The delivery device 128 is a suturing device that can be used to pass an end of a leader or implant through a pelvic tissue. Such a delivery device 128 is also described in U.S. Pat. No. 5,741,277 to Gordon et al. ("the Gordon patent"), and U.S. Pat. No. 7,122,039 to Chu ("the Chu patent"), the disclosures of which are hereby incorporated by reference in their entirety. The delivery device 128 includes a shaft body 158, a carrier 162 and a catch 160. The structure and use of delivery device 128 is described in more detail in the Gordon patent and the Chu patent referenced above.

To prepare a patient for deployment of the implant 120 with a delivery device 128, the patient can be given an injection of local anesthesia, for example, along a medial aspect of the obturator foramina and anterior wall of the vagina. An incision can be made along an anterior vaginal mucosa. The incision can be, for example, 1.5 to 2.0 cm (0.6 to 0.8 inches) in length and can extend approximately 0.5 cm (0.2 inches) to the meatus. The vaginal epithelium is dissected from the underlying periurethral fascia. The internal edge of an obturator foramen can be identified through palpation, for example at the level of the clitoris.

To deliver an implant to a pelvic region using the delivery device 130, the trocar 140 of the dilator 130 can be loaded into the catch 160 of the delivery device 128. The delivery device 128 can then be used to pass the trocar needle 140 and the dilator 130 through a pelvic tissue. Specifically, the carrier 162 of the delivery device 128 is positioned adjacent a selected tissue site and the carrier 162 is fired such that the trocar needle 140 pierces through the tissue. The trocar needle 140 and distal end portion 144 of the leader 142 are retrieved by the catch 160 after passing through the tissue. The distal end portion 144 of the leader 142 are removed from the catch 160 and the dilator 130 is pulled partially through the tissue. This procedure is then repeated for other dilators that are coupled to other straps of the implant. Each strap of the implant are pulled through a selected tissue site and the straps are adjusted to position the implant. The straps can then be cut to decouple the straps from the dilator.

Figure 6:
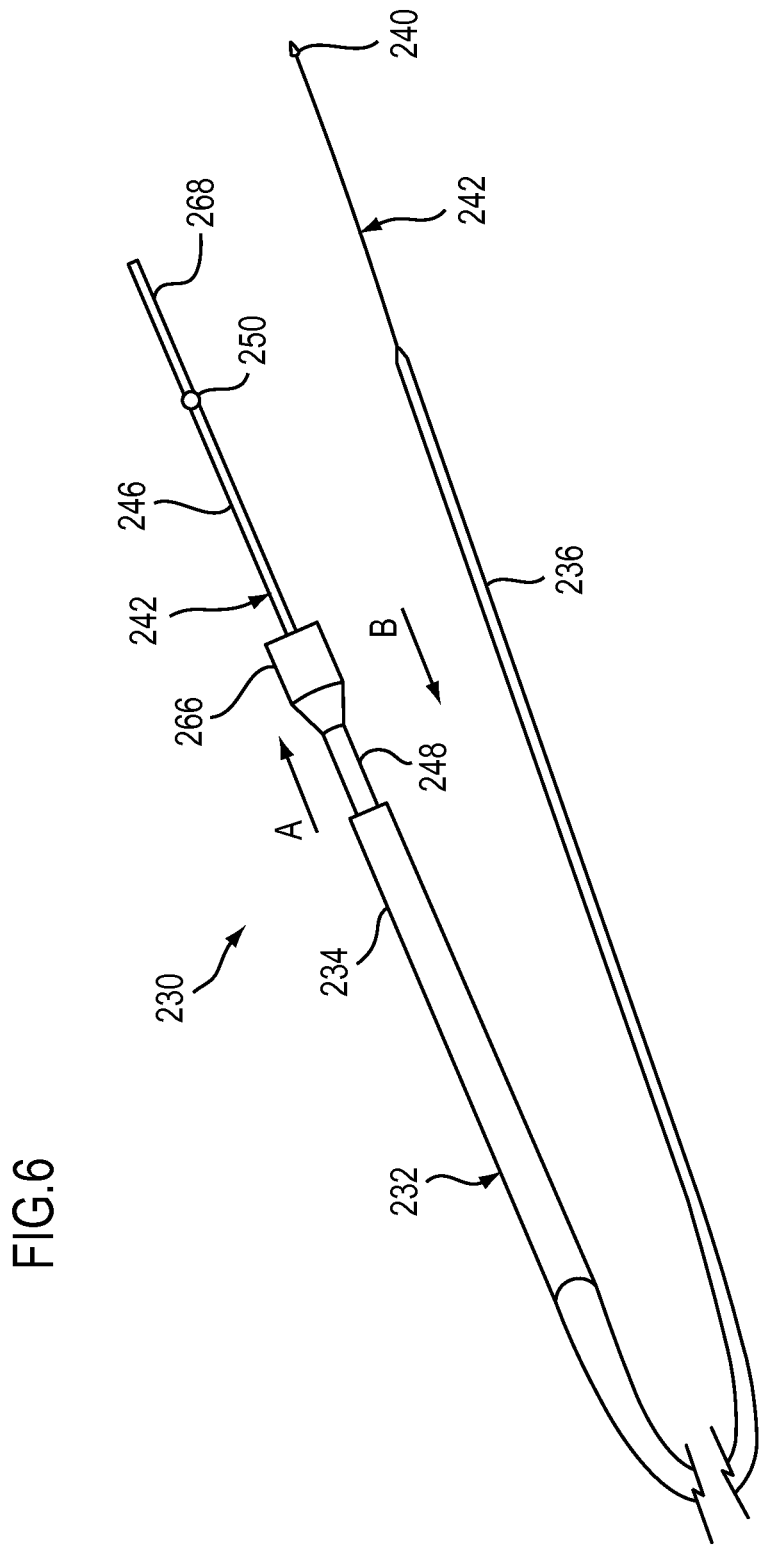
FIG. 6 is a top view of an embodiment of another dilator device shown in a first configuration.
Figure 7:
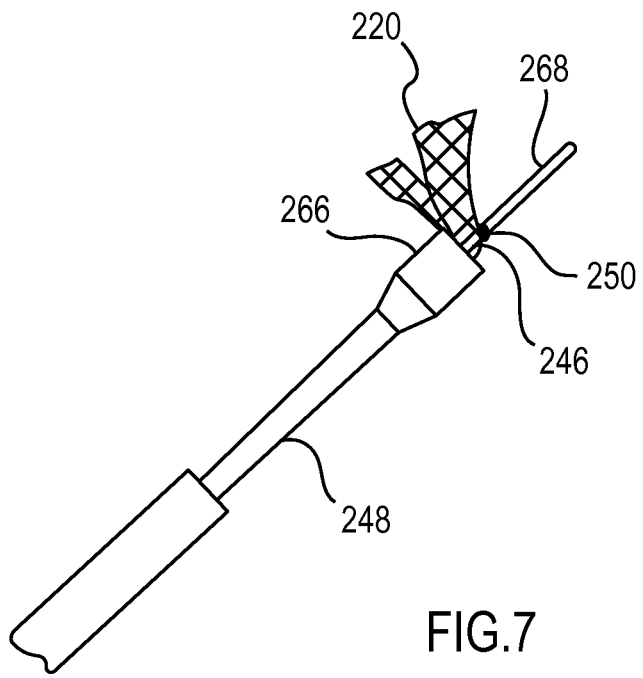
FIG. 7 is a top view of a proximal end portion of the dilator device of FIG. 6 shown in a second configuration.

FIG. 6 illustrates another embodiment of a dilator device. A dilator device 230 is similarly constructed as the dilator 130 and can be used in a similar manner to deliver an implant to a pelvic region. The dilator 230 includes an elongate body 232, a leader 242 and a lock tube 248. In this embodiment, the lock tube 248 is tapered and includes a cup portion 266. A strap of an implant (not shown in FIG. 6) can be placed through a loop 246 formed in the leader 242. A stop member 250 in the form of a bead that can slide on the loop 246 to tighten the loop 246 around the strap of the implant. The lock tube 248 can be coupled to the elongate body 232 in a similar manner as described for the previous embodiment, such that the lock tube 248 can move relative to the elongate body 232. In this embodiment, when the lock tube 248 is moved in the direction of arrow A, the cup portion 266 slides over the portion of the implant strap within the loop 246. FIG. 7 illustrates a portion of an implant 220 placed within the loop 246 and the cup portion 266 of the lock tube 248 disposed over a portion of the loop 246 and the implant 220. To release the portion of the implant 220 from the dilator 230, a handle portion 268 of the loop 246 can be held while at the same time the lock tube 248 is moved in the direction of arrow B (FIG. 6).

Figure 8:
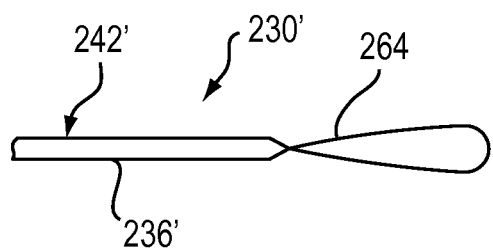
FIG. 8 is a top view of a distal end portion of another embodiment of a dilator device.

The dilator 230 also includes a trocar needle 240 coupled to a distal end of the leader 242. As with the previous embodiment, the trocar needle 240 can be used to releasably couple the dilator 230 to a delivery device, such as delivery device 128. In an alternative embodiment, the leader can form a loop at a distal end of the dilator, or another connector can be coupled to a distal end of the dilator, which can be used to releasable couple the dilator to a different type of delivery device. For example, as shown in FIG. 8, a loop connector 264 can be coupled to a distal end portion 236' of an elongate body 232'. The loop connector 264 can be releasably coupled to a delivery device 228 illustrated in FIG. 9. The loop connector 264 can be, for example, a portion of the leader (e.g., suture) that extends from the distal end of the dilator.

Figure 9:
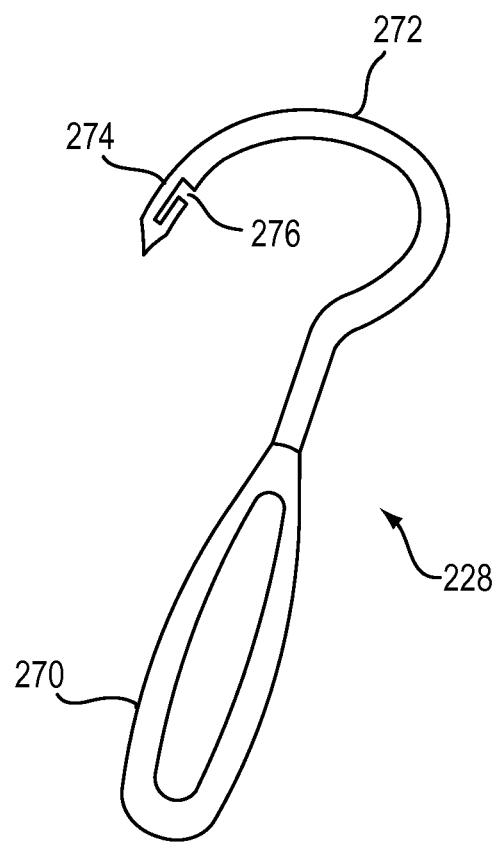
FIG. 9 is a side view of another embodiment of a delivery device.

The delivery device 228 includes a handle 270, a curved shaft 272, and a connector end 274. The connector end 274 defines a notch 276 that is configured to receive the loop connector 264 of dilator 230'. The delivery device 228 can be, for example, an Obtryx® Curve device, an Obtryx® Halo device, a Curve, or a Lynx® device all manufactured by Boston Scientific Corporation. An example of such a device is also described in U.S. Patent Pub. No. 2005/0075660 and U.S. Patent Pub. No. 2005/0177022, the entire disclosures of which are hereby incorporated by reference in their entirety. Although the delivery device 228 is shown having a curved shaft 272, in other embodiments, the shaft is substantially straight, angled or curved at a different radius of curvature than as shown in FIG. 9. The delivery device 228 can be used, for example, to deliver anterior straps of a pelvic implant.

It should be understood that the delivery device 228 is merely an example of the type of delivery device that can be used to deliver the dilator 230' to a desired location within a pelvic region of a patient. For example, in some embodiments, a tube shaped connector is coupled to the distal end of the elongate body of the dilator to associate the dilator to a delivery device such as those used in the Advantage® or Prefyx™ systems manufactured by Boston Scientific Corporation. Such a device can be used, for example, to deliver a portion of an implant in a retro pubic or pre-pubic approach.

Figure 10:
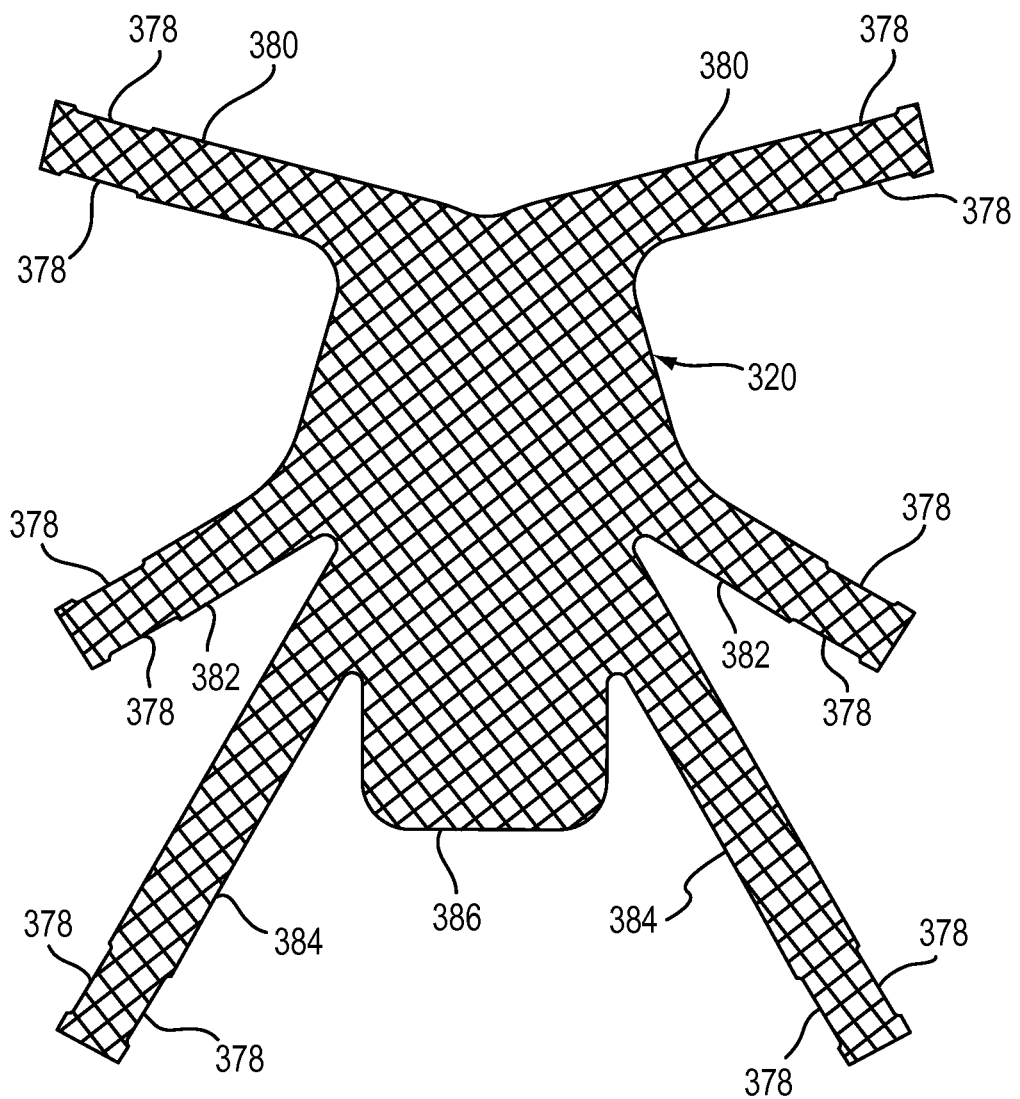
FIG. 10 is a top view of an embodiment of an implant.
Figure 11:
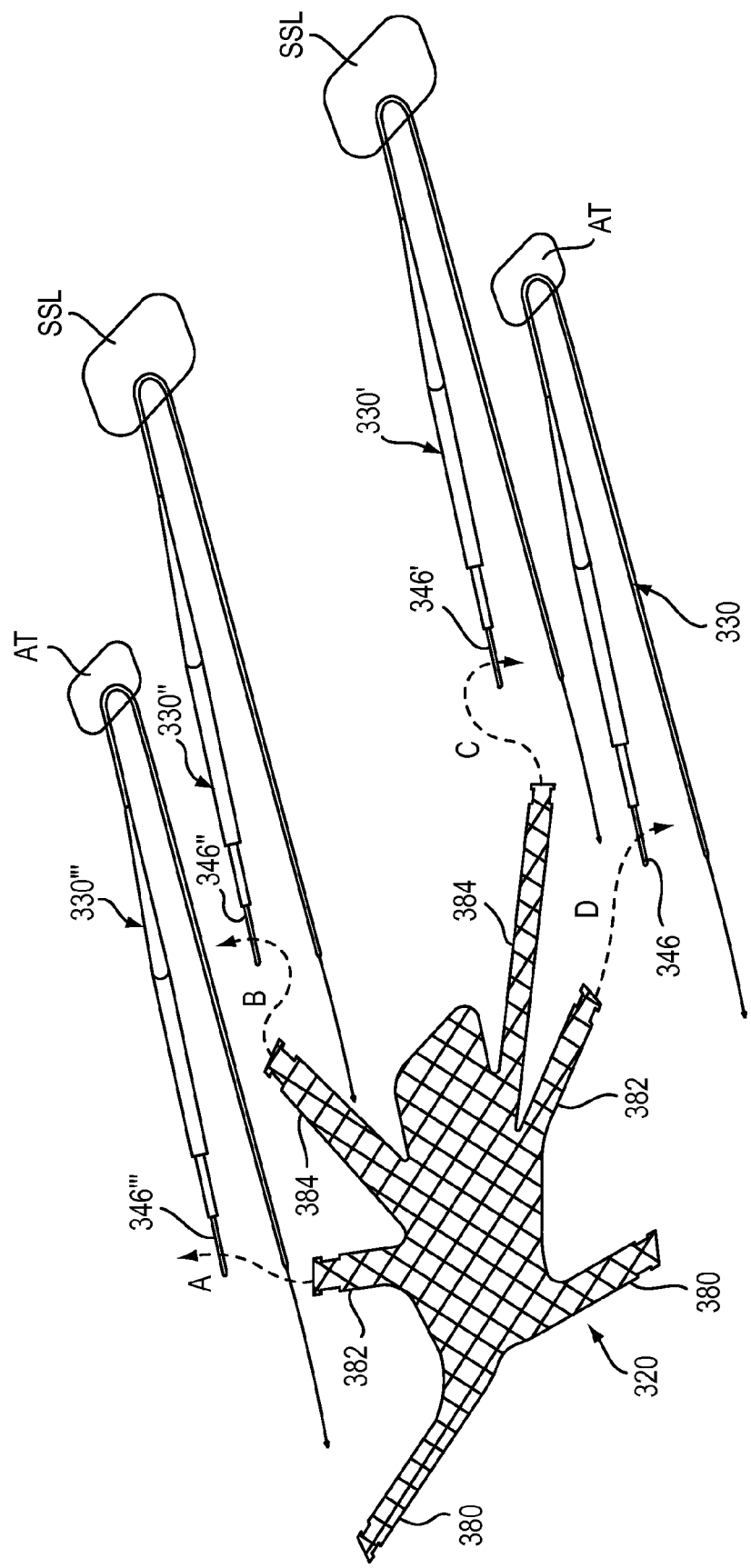
FIG. 11 is a side perspective view of four dilator devices and the implant of FIG. 10 shown disposed within a schematic illustration of a portion of a pelvic region.

FIG. 10 illustrates an example of an anterior pelvic floor implant. An implant 320 includes multiple pairs of straps 380, 382 and 384, and an anterior support portion 386. Each of the straps 380, 382, 384 can be associated to a dilator device as described herein. Each of the straps 380, 382, 384 include a grooved portion 378. The grooved portions 384 indicate a location to associate the strap to a loop of a dilator. FIG. 11 illustrates four dilators 330, 330', 330", 330''' that can be used to deliver straps of an implant. Dilators 330 and 330''' are each shown passed through a schematic representation of an arcus tendineus (AT). Dilators 330' and 330" are each shown passed through a schematic representation of a sacrospinous ligament (SSL). The dilators can be passed through the various tissue locations, for example, using a delivery device, such as delivery device 128 described herein.

The implant 320 can be delivered to a pelvic region using the dilators of FIG. 11 by associating the various straps of the implant 320 to a selected dilator and using the dilator to pass the strap through the selected tissue portion. For example, as shown in FIG. 11, the straps 384 can be placed through the loops 346' and 346" as indicated by the dotted line arrows B and C, and secured to the dilators 330' and 330", respectively. The straps 382 of the implant 320 can be similarly secured to the dilators 330 and 330''' by passing the straps 382 through the loops 346 and 346''' as indicated by the dotted line arrows A and D and secured to the dilators 330 and 330'''. The dilators can then be used to pull the respective straps through the sacrospinous ligaments and the arcus tendineus as indicated in FIG. 11. Although not shown in FIG. 11, the straps 380 can be delivered into a pelvic region and through a tissue in a similar manner. For example, the straps 380 can be coupled to a dilator device and pulled through an obturator membrane using a delivery device, such as delivery device 128. In some embodiments, a connector can be coupled to the straps 380 such that the straps 380 can be delivered using a delivery device, such as delivery device 228 shown in FIG. 9.

Figure 12:
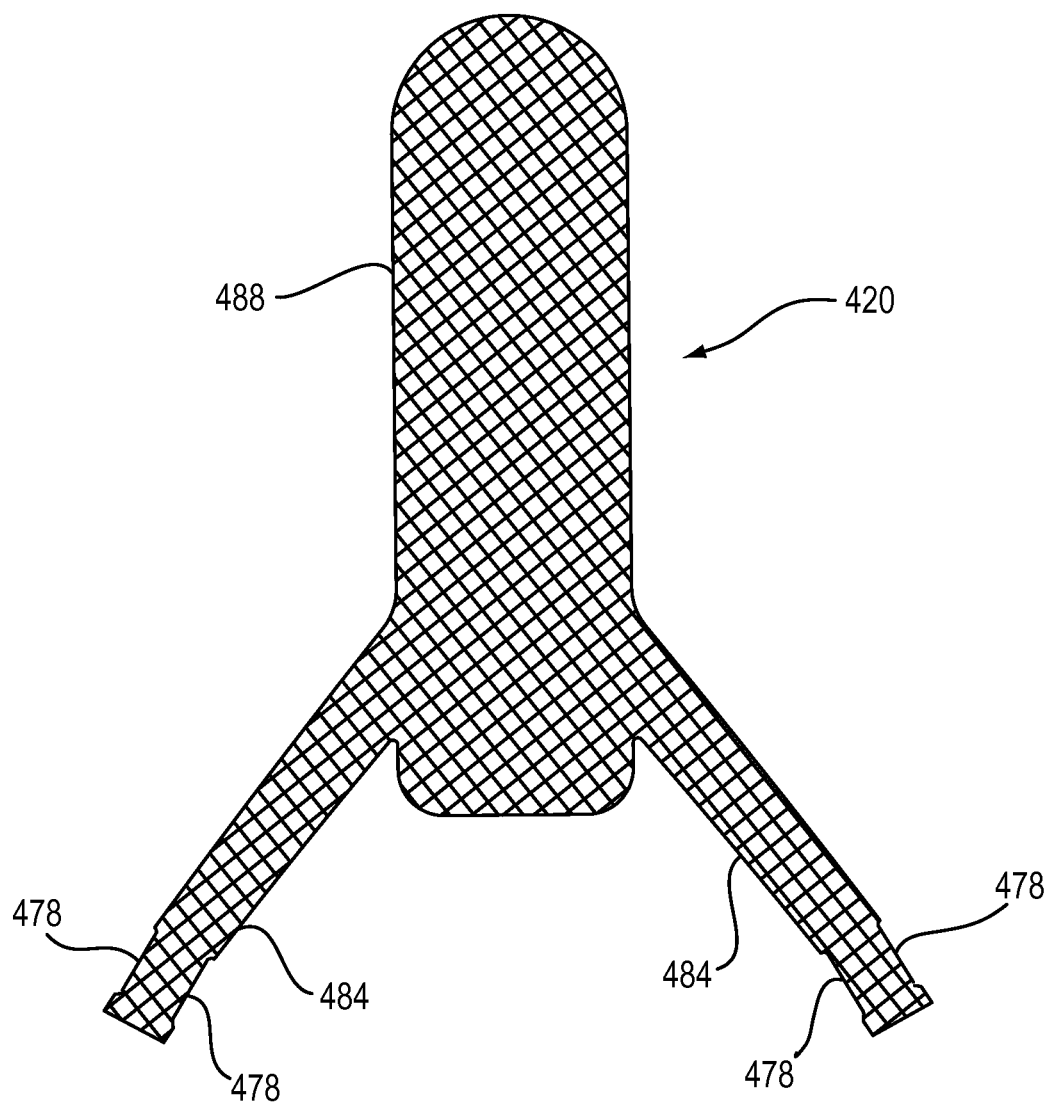
FIG. 12 is a top view of an embodiment of an implant.
Figure 13:
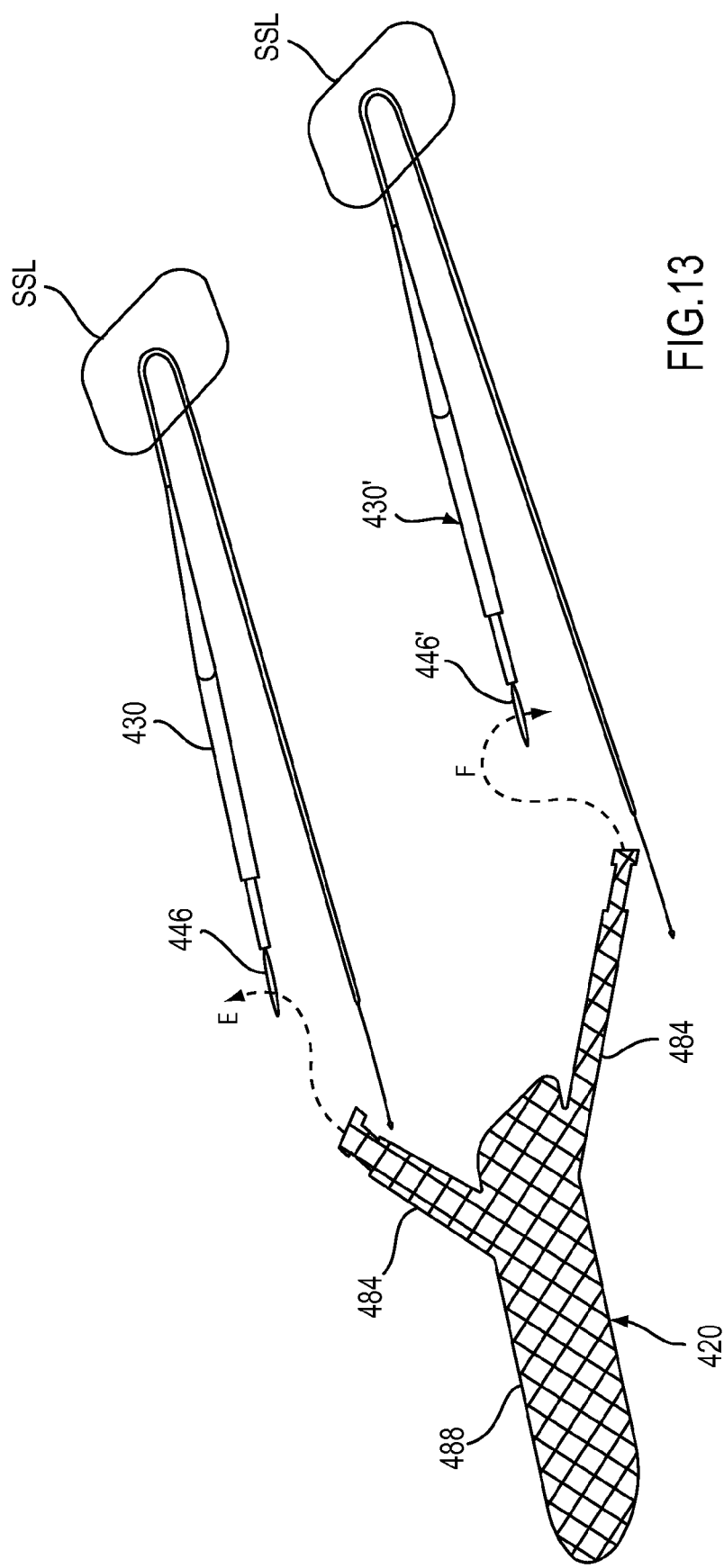
FIG. 13 is a side perspective view of a pair of two dilator devices and the implant of FIG. 12 shown disposed within a schematic illustration of a portion of a pelvic region.

FIG. 12 illustrates an example of a posterior implant that can be delivered to a pelvic region using the dilator devices described herein. An implant 420 includes a support portion 488 and a pair of straps 484. The straps 484 each have grooved portions 478 to indicate a location to place the straps 484 through a loop of a dilator as described previously. The straps 484 can be delivered, for example, through a sacrospinous ligament. FIG. 13 illustrates a pair of dilators 430 and 430' after being passed through a schematic representation of sacrospinous ligaments SSL using for example, a delivery device 128. For example, the dilators 430 and 430' can be passed through a posterior vaginal incision. The straps 484 can be placed through a loop 446 and 446' of the respective dilator 430 and 430' s indicated by the arrows E and F respectively. The dilators 430 and 430' can then be used pull the straps 484 through the sacrospinous ligaments.

Figure 14:
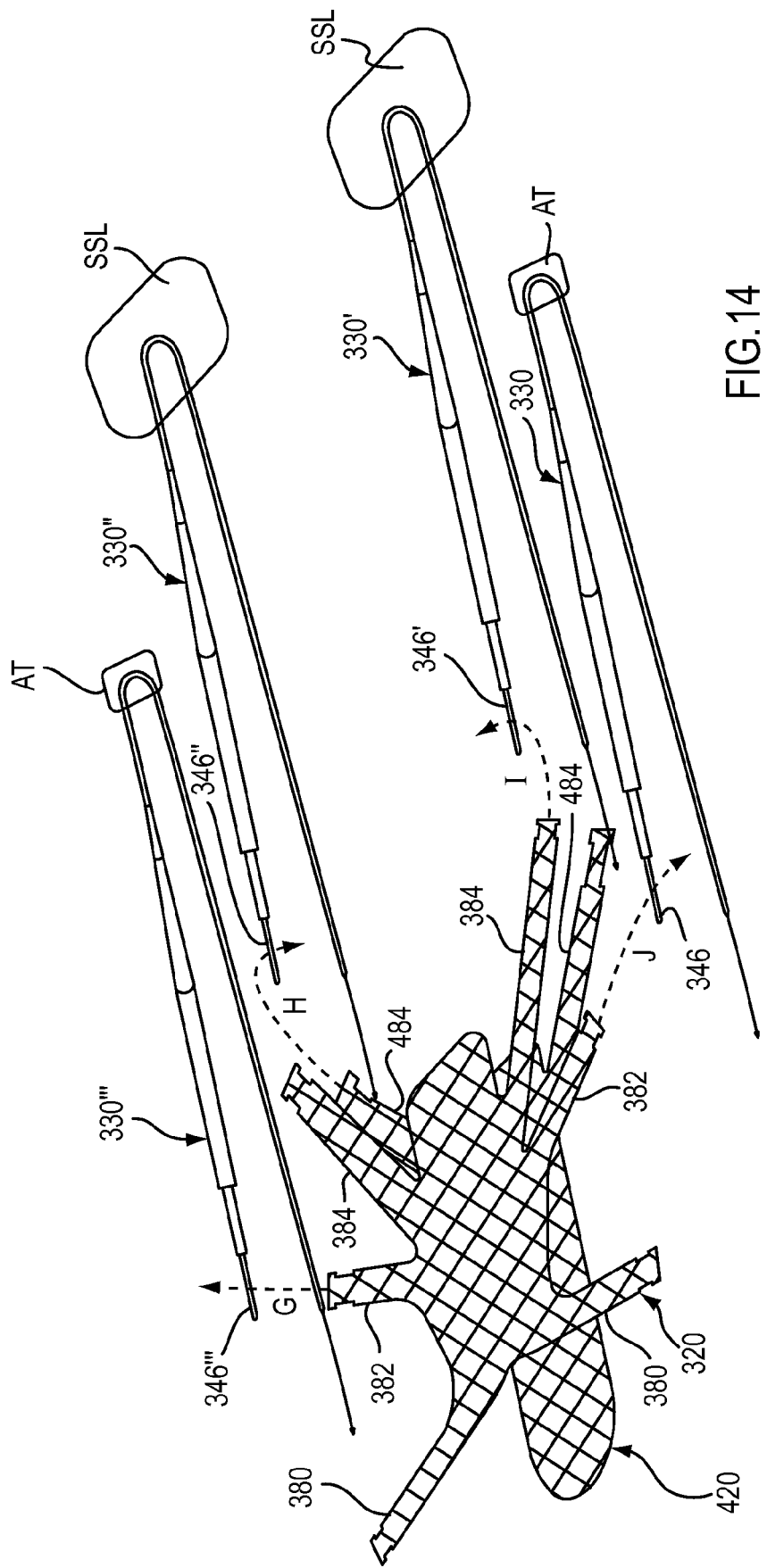
FIG. 14 is a side perspective view of four dilator devices and the implants of FIGS. 10 and 12 shown disposed within a schematic illustration of a portion of a pelvic region.

FIG. 14 illustrates the use of dilators to deliver both the anterior implant 320 and the posterior implant 420 at the same time. A schematic representation of the sacrospinous ligaments SSL and the arcus tendineus AT are also illustrated in FIG. 14. The straps 384 on implant 320 and the straps 484 on implant 420 are combined and placed through the loops 346" and 346' on the dilators 330" and 330', respectively, as indicated by the dashed-line paths of the arrows H and I, respectively. The straps 384, 484 can then be secured to the dilators 330", 330' as previously described. The dilators 330" and 330' can then be used to pull the straps 384 and 484 through the sacrospinous ligaments SSL on each side of a pelvic region. Placing two straps (e.g. 384, 484) through the SSL with one dilator at the same time reduces the procedure time as well as reduces damage to the SSL during the delivery process. The dilators can be placed in the SSL by either an anterior or posterior vaginal incision.

The straps 382 of the implant 320 can be placed through the loops 346''' and 346 of the dilators 330''' and 330, respectively, as indicated by the dashed-line paths of the arrows G and J, respectively. The straps 382 can be secured to the dilators 330, 330''' as previously described. The dilators 330''' and 330 can then be used to pull the straps 382 through the arcus tendineus AT on each side of a pelvic region. The straps 380 can be delivered in a similar manner as described above with reference to FIG. 11.

Figure 15:
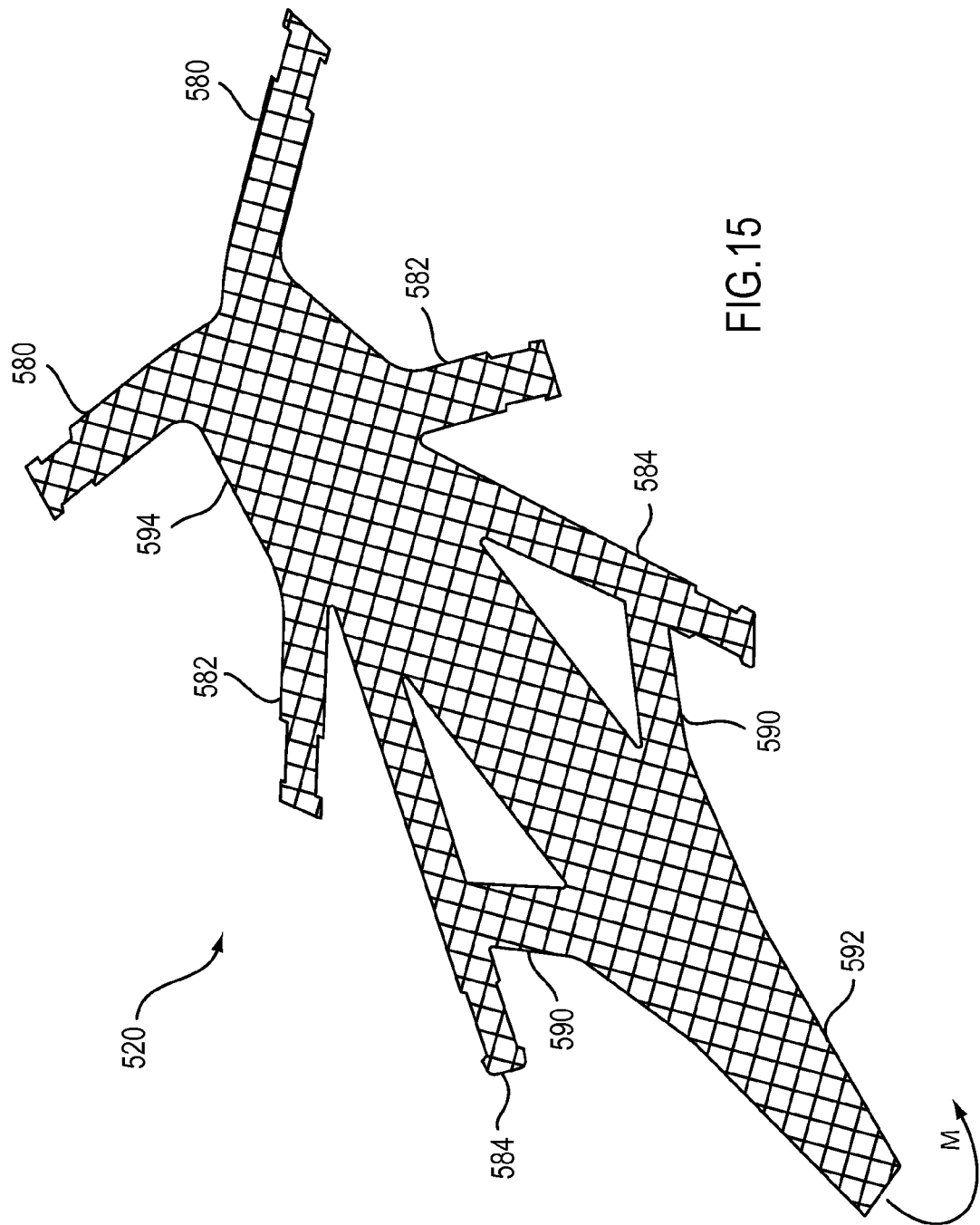
FIG. 15 is a side perspective view of an embodiment of an implant.

FIG. 15 illustrates an example of a total pelvic floor repair implant where the straps of the implant to be placed through an SSL of an anterior portion of the implant are connected to straps to be placed through the SSL of the posterior portion of the implant. An implant 520 includes a posterior support portion 592 and an anterior support portion 594. A pair of straps 584 are connected to branch portions 590 that extend from the posterior support portion 592. The straps 584 can be releasably coupled to a dilator as described herein and the dilator can be used to pull both the straps 584 and the branch portions 590 through, for example, through a sacrospinous ligament. The implant 520 also includes straps 582 and 580. The straps 582 can each be coupled to a dilator device and delivered through, for example, an arcus tendineus, as described for previous embodiments. Likewise, straps 580 can each be coupled to a dilator device and delivered through, for example, an obturator membrane as described previously.

The combined posterior portion of the implant 520 can be used, for example, to provide support to both the anterior portion 594 and posterior portion 592 of the implant 520. The anterior support portion can be secured, for example, to pelvic fascia or to the vaginal cuff to complete the apical support. The posterior portion 592 of the implant 520 can be tucked or secured, for example, with sutures, into a posterior vaginal compartment to provide posterior support. For example, the posterior portion 592 can be tucked in a direction of arrow M shown in FIG. 15.

Figure 18:
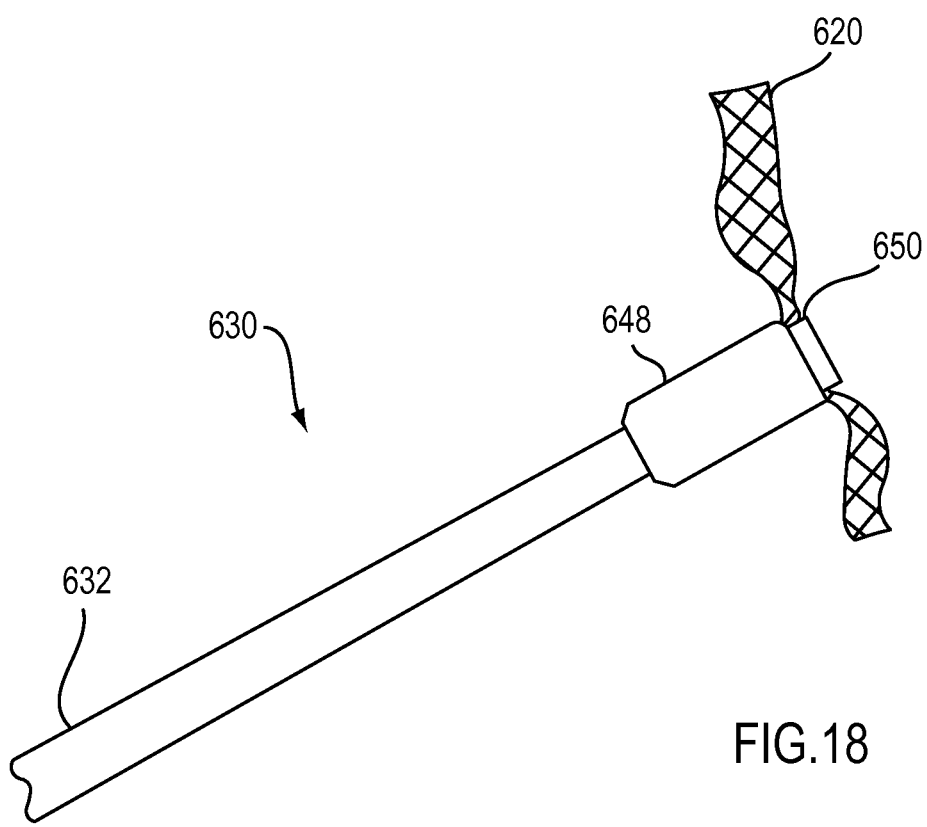
FIG. 18 is a side perspective view of the portion of the dilator device and implant of FIG. 17, shown with the lock tube in a second position.

FIGS. 16-18 illustrate a portion of a dilator device according to another embodiment. A dilator 630 includes an elongate body 632 and a lock tube 648 (FIG. 17). Only a proximal end portion 634 of the elongate body 632 is shown in FIG. 16. The elongate body 632 and lock tube 648 are shown in FIG. 17. It should be understood, however, the dilator 630 can include components described in previous embodiments, such as, a leader and trocar needle, or other connector at a distal end portion, to associate the dilator 630 to a delivery device.

The elongate body 632 has a closed or collapsed configuration as shown in FIG. 16 and an expanded or open configuration as shown in FIG. 17. A slit 696 is formed through walls of the elongate body 632 as shown in FIG. 16. The elongate body 632 can be formed such that it is biased into the open configuration. For example, the elongate body 632 can be heat set, or formed of shape-memory material to bias the elongate body 632 into the open configuration, shown in FIG. 17. As shown in FIG. 17, in the open configuration, the slit 696 forms an opening 698 in the elongate body 632, through which an implant 620, or a portion of an implant, such as a strap, can be placed. The lock tube 648 is slidably disposed over an outer surface of the elongate body 632 and can be used to move the elongate body 632 between the collapsed configuration and the open configuration. To secure the implant 620 to the dilator 630, the lock tube 648 is slid in the direction of arrow M, which collapses the proximal end portion 634 to the closed configuration and traps or secures a portion of the implant 620 within a lumen (not shown) of the lock tube 648 as shown in FIG. 18.

Figure 21:
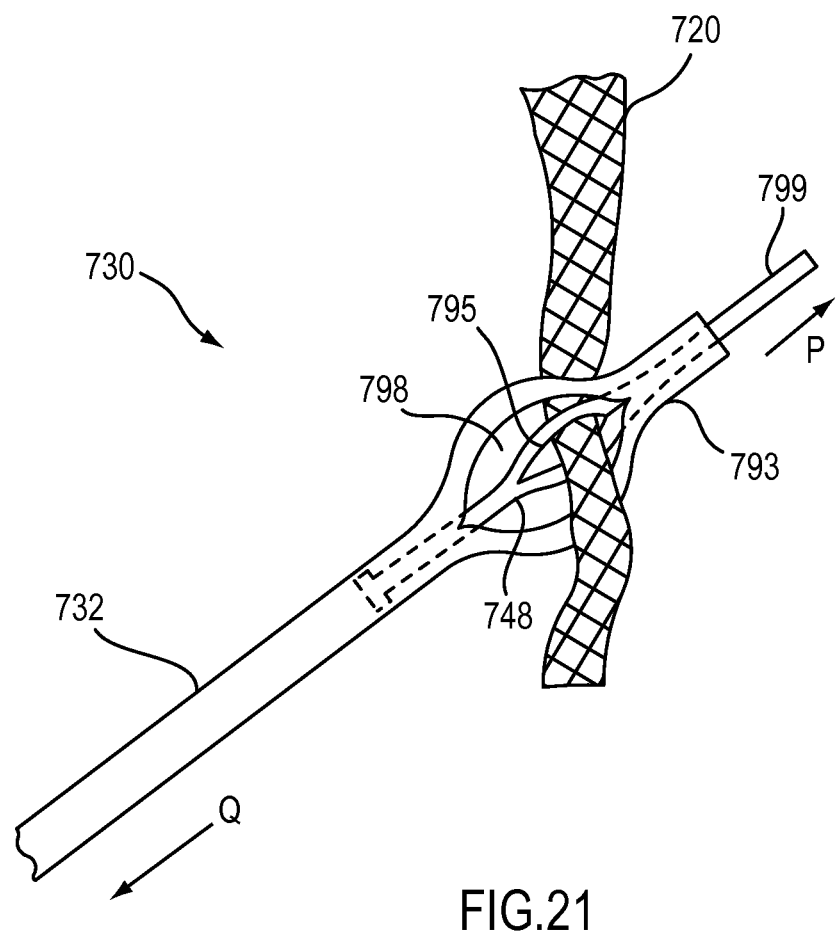
FIG. 21 is a side perspective view of the portion of the dilator device and implant of FIG. 20, shown in a partially collapsed configuration.

FIGS. 19-21 illustrate a portion of another embodiment of a dilator. A dilator 730 includes an elongate body 732 and a lock tube 748. The elongate body 732 has a longitudinal slit 796 formed in a wall of the elongate body 732 as in the previous embodiment. In this embodiment, the lock tube 748 also has a longitudinal slit 797 formed in a wall of the lock tube 748 as shown in FIG. 19. The lock tube 748 is sized such that the lock tube 748 can be slidably received within a lumen (not shown) of the elongate body 732. FIG. 19 shows the lock tube 748 partially disposed within the lumen of the elongate body 732 and partially extending outside of the elongate body 732 to show the slit 797. The lock tube 748 is placed within the lumen of the elongate body 732 such that the slits 796 and 797 are aligned, and the combined structure is heat or thermo set such that each of the elongate body 732 and the lock tube 748 are biased into an open or expanded configuration as shown in FIG. 20. In the expanded configuration, the elongate body 732 defines an opening 798 (shown in FIG. 21) and the lock tube 748 defines an opening 795 (shown in FIGS. 20 and 21).

As shown in FIG. 20, when the lock tube 748 and the elongate body 732 are each in the expanded configuration, the opening 795 of the lock tube 748 is substantially aligned with the opening 798 of the elongate body 732 as shown in FIG. 20. A portion of an implant 720, such as a strap, can then be placed through the opening 795 of the lock tube 748, accessible through the opening 798 of the elongate body 732. To secure the implant 720 to the dilator 730, an end portion 799 of the lock tube 748 is pulled in a direction of arrow P such that the opening 795 of the lock tube 748 at least partially closes against the implant 720, as shown in FIG. 21. Specifically, as the lock tube 748 is pulled in the direction of arrow P, the portion of the lock tube 748 that defines the opening 795 will be pulled into an end portion 793 of the elongate body 732, which will apply a force to the outer walls of the lock tube 748 and move the lock tube 748 to a collapsed configuration.

The lock tube 748 includes a stop member 750 at a distal end portion of the lock tube 748 to limit the travel of the lock tube 748 relative to the elongate body 732 and ensure that the lock tube 748 does not slide completely outside of the elongate body 732. For example, as the lock tube 748 is moved in the direction of arrow P, the stop member 750 can engage a flange on the end portion 793 (not shown).

During placement of the dilator 730 within a pelvic tissue, as the dilator 730 is pulled in the direction of arrow Q (FIG. 21), the opening 798 of the elongate body 732 will at least partially collapse to allow the dilator 730 to pass through the tissue. For example, the force of the tissue against the outer surface of the elongate body 732 will cause the elongate body 732 to move to a collapsed configuration (not shown).

Figure 22:
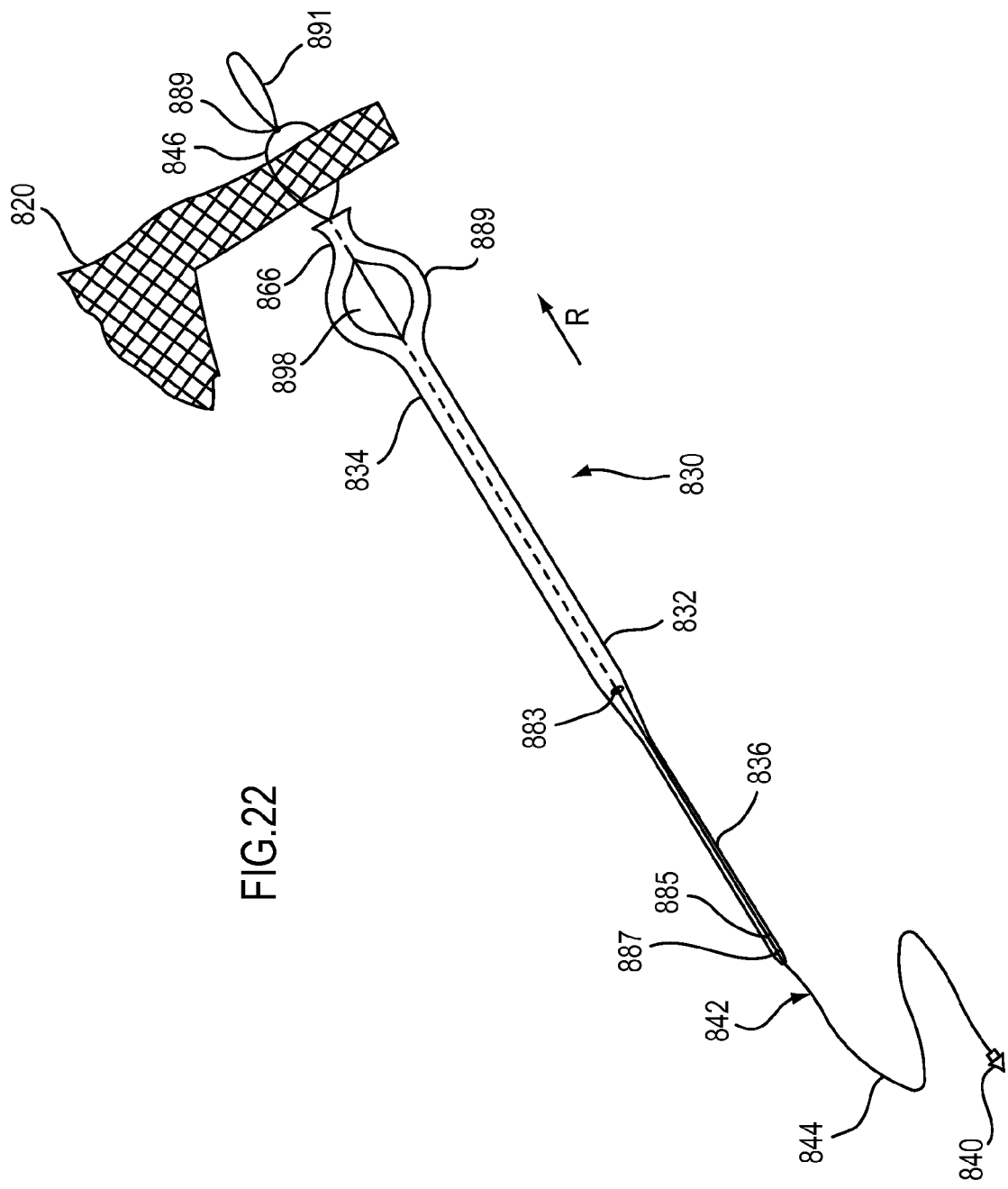
FIG. 22 is a side perspective view of another embodiment of a dilator device shown in an expanded configuration and a portion of an embodiment of an implant.
Figure 23:
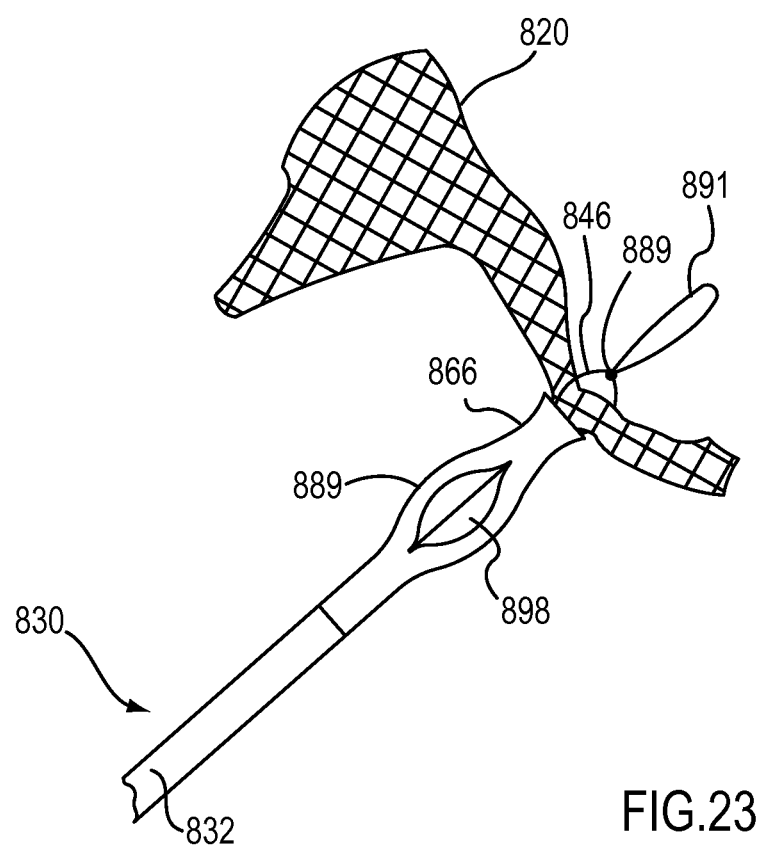
FIG. 23 is a side perspective view of the portion of the dilator device and implant of FIG. 22 shown in a partially collapsed configuration.

FIGS. 22 and 23 illustrate another embodiment of a dilator device. A dilator 830 includes an elongate body 832 and a leader 842. The elongate body 832 is similar to the previous embodiments and includes a proximal end portion 834 and a distal end portion 836. The elongate body 832 tapers from a larger outer diameter at the proximal end portion 834 to a smaller outer diameter at the distal end portion 836. The elongate body 832 also defines an opening 898 that can be formed as described above for previous embodiments. For example, a slit can be cut through an outer wall of the elongate body 832 and the elongate body 832 can then be heat set such that the elongate body 889 is biased into an open or expanded configuration defining the opening 898 in a portion 889 of the elongate body 832. The proximal end portion 834 also includes a flared or cup portion 866.

The leader 842 extends through a lumen (not shown) of the elongate body 832. A distal end portion 844 of the leader 842 extends from the distal end portion 836 of the elongate body 832. A trocar needle 840 is coupled to the distal end portion 844 as shown in FIG. 22. A proximal end portion of the leader 842 extends from the proximal end portion 834 of the elongate body 832 and forms a first loop 846. The leader 842 also has a second loop 891 formed adjacent to the first loop 846. For example, a knot 898 can be formed in the leader 842 as shown in FIG. 22. The elongate body 832 can be coupled to the leader 842 by thermal bonding the distal end portion 836 of the elongate body 832 to knots 887 and 885 formed in the leader 842. For example, the elongate body 832 can be thermal bonded to the leader 842 during the forming process of the elongate body 832. Additional knots can also be used to secure the leader 842 to the elongate body 832, such as the knot 883 shown in FIG. 22.

A portion of an implant 820 is shown with a strap of the implant 820 placed through the first loop 846. The second loop 891 can be used as a handle to assist in placing the strap through the first loop 846. The cup portion 866 of the elongate body 832 can be used to at least partially encapsulate the strap of the implant 820. To secure the strap of the implant 820 to the dilator 830, the cup portion 866 is manually moved by the user (e.g., by hand) in a direction of arrow R, while simultaneously manually collapsing the portion 889 of the elongate body 832 (e.g., the user can squeeze the portion 889) such that the opening 898 is at least partially closed or collapsed. This will extend the portion 889 in the direction of arrow R and the cup portion 866 over the portion of the strap of the implant 820 placed through the first loop 846.

FIG. 23 illustrates the portion 889 partially collapsed and the cup portion 866 partially covering the strap of the implant 820. The engagement between the strap of the implant 820 and interior walls of the cup portion 866 will hold the portion 889 in the partially collapsed position. With the strap of the implant 820 coupled to the dilator 830, the dilator 830 can be used to deliver the strap of the implant 820 through a tissue site as described for previous embodiment.

Figure 24:
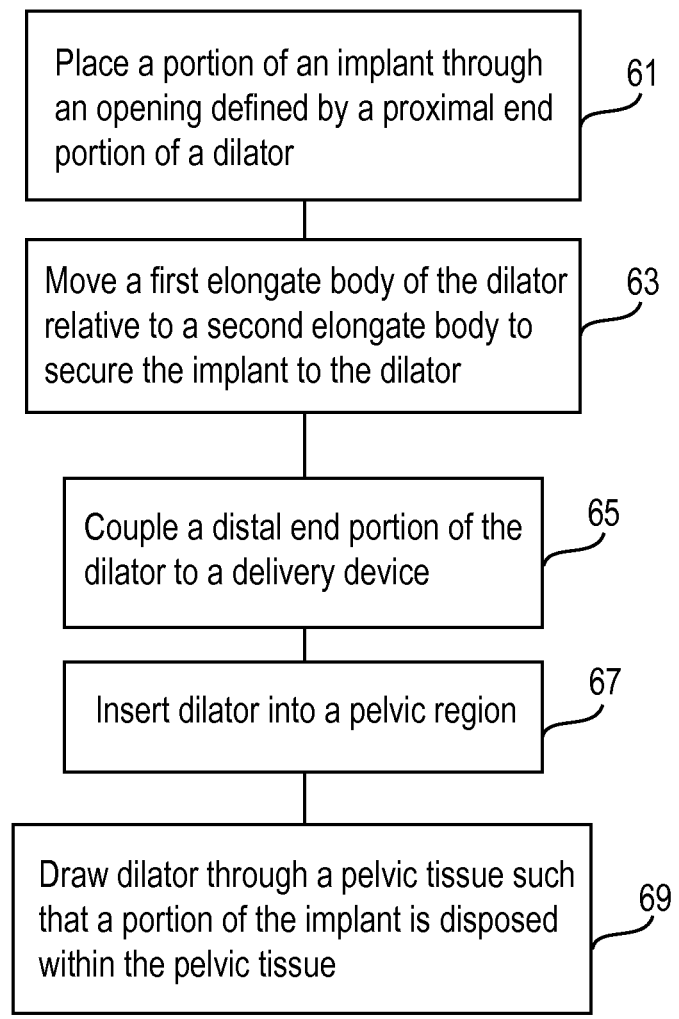
FIG. 24 is a flowchart illustrating an embodiment of a method.

FIG. 24 is a flowchart of a method according to one embodiment of the invention. The method includes at 61, placing a portion of an implant through an opening defined by a proximal end portion of a dilator. In some embodiments, the opening can be defined, for example, by a suture coupled to the second elongate body. In another embodiment, the opening can be defined, for example, by the second elongate body. At 63, a first elongate body of the dilator is moved relative to a second elongate body of the dilator to secure the implant to the dilator. In some embodiments, the first elongate body is movably disposed within a lumen of the second elongate body. In some embodiments, the second elongate body is movably disposed within the first elongate body. In some embodiments, the first or second elongate body is a lock tube.

At 65, a distal end portion of the dilator is coupled to a delivery device that can be used to deliver the dilator and implant through a pelvic tissue. At 67, the dilator can be inserted into a pelvic region. The dilator can be inserted into the pelvic region either before or after placement of the implant through the opening on the dilator. At 69, the dilator can be drawn through a pelvic tissue such that a portion of the implant is disposed within the pelvic tissue.

The various components of the dilator devices (e.g., 130, 230, 330, etc.) described herein can be formed with a variety of different biocompatible plastics and/or metals. For example, the elongate body and the lock tubes of the dilator devices described herein can be formed with various materials, such as a polymer. In addition, the elongate body and lock tubes of the dilator devices can be formed with a molding or extrusion process. The leader can be various materials as described herein and can be a suitable suture material used for such medical procedures.

The dilator devices described herein can be used to deliver and place a variety of different implants not specifically described. The implants described herein (e.g., implant, 20, 120, 220, 320 etc.) can be formed with a variety of different materials, such as biocompatible plastics and/or metals. In some embodiments, the implant is formed with a mesh material to promote tissue in-growth. For example, the Advantage® Mesh manufactured by Boston Scientific Corporation can be used. Alternatively, the implant can be formed, for example, with Polyform® mesh material manufactured by Boston Scientific Corporation. The implant can also be formed with materials such that it is disposable. For example, the implant can be formed with materials such that a single use of the device is contemplated.

In one embodiment, an apparatus includes an elongate body having a distal end configured to releasably couple the elongate body to a delivery device. A lock tube is movably disposable within a lumen of the elongate body. A connector is disposed at a proximal end of the elongate body that is configured to releasably couple a pelvic implant to the elongate body. The lock tube is configured to be slidably moved to a position adjacent the pelvic implant to secure the pelvic implant to the elongate body. In some embodiments, the apparatus also includes a trocar coupled to the distal end of the elongate body and configured to releasably couple the elongate body to the delivery device. In some embodiments, the apparatus includes a stop member coupled to the lock member and configured to limit the travel of the lock tube relative to the elongate body. In some embodiments, the connector is a loop. In some embodiments, the apparatus further includes a flange disposed within the lumen of the elongate body that is configured to limit the travel of the lock tube relative to the elongate body. In some embodiments, the apparatus further includes a connector at a distal end of the elongate body that is configured to releasably couple the elongate body to a delivery device. In some embodiments, the lock tube includes a cup portion configured to be disposed over a portion of a pelvic implant when the pelvic implant is coupled to the elongate body.

In another embodiment, an apparatus includes an elongate body movable between an expanded configuration and a collapsed configuration. The elongate body in the expanded configuration defines an opening at a proximal end portion of the elongate body that is configured to receive a portion of a pelvic implant therethrough. A lock member is slidably disposed over at least a portion of the elongate body. The lock member is configured to move between a first position in which the elongate body is in the expanded configuration and a second position in which the elongate body is in the collapsed configuration and the opening of the elongate body is at least partially disposed within a lumen of the lock member. In some embodiments, the lock member includes a cup portion configured to be disposed over the opening of the elongate body when the lock member is in the second position. In some embodiments, the apparatus also includes a connector at a distal end of the elongate body that is configured to releasably couple the elongate body to a delivery device. In some embodiments, the elongate body includes a flange at a proximal end portion that is configured to limit travel of the lock member relative to the elongate body. In some embodiments, the apparatus also includes a leader coupled to a distal end of the elongate body and a trocar needle coupled to the leader that is configured to releasably couple the elongate body to a delivery device.

In another embodiment, an apparatus includes a first elongate body and a second elongate body. The first elongate body has an expanded configuration and a collapsed configuration. In its expanded configuration, the first elongate body defines an opening on a proximal end portion of the elongate body. The second elongate body is at least partially disposed within a lumen of the first elongate body and has an expanded configuration and a collapsed configuration. The second elongate body in its expanded configuration defines an opening on a proximal end portion of the second elongate body. When in its expanded configuration, the second elongate body is configured to receive at least a portion of an implant through its opening. When in its collapsed configuration, the second elongate body is configured to secure the pelvic implant to the apparatus. In some embodiments, the second elongate body includes a handle portion at a proximal end of the second elongate body and the handle portion is outside of the lumen of the first elongate body. In some embodiments, the second elongate body can be positioned relative to the first elongate body such that the opening of the second elongate body is accessible through the opening of the first elongate body. In some embodiments, the apparatus further includes a leader coupled to a distal end of the first elongate body and a trocar needle coupled to the leader that is configured to releasably couple the first elongate body to a delivery device. In some embodiments, the first elongate body includes an end portion disposed proximal of the opening of the first elongate body, and the end portion of the first elongate body is configured to move the second elongate body from its expanded configuration to its collapsed configuration. In some embodiments, the first elongate body is configured to be moved to its collapsed configuration as the apparatus is moved through a tissue. In some embodiments, the second elongate body includes a stop member configured to limit travel of the second elongate body relative to the first elongate body. In some embodiments, the first elongate body includes a flange at a proximal end configured to limit travel of the second elongate body.

In another embodiment, a method includes placing a portion of an implant through an opening defined by a proximal end portion of a dilator, and moving a first elongate body of the dilator and a second elongate body of the dilator relative to each other to secure the implant to the dilator. In some embodiments, the opening is defined by a suture that is coupled to the second elongate body and the first elongate body is slidably moved within a lumen defined by the second elongate body to a position adjacent the implant. In some embodiments, the opening is defined by the second elongate body and the first elongate body is moved over the second elongate body such that the first elongate body is disposed at least partially over the opening of the second elongate body. In some embodiments, the opening is defined by the second elongate body and the second elongate body is slidably moved within a lumen defined by the first elongate body such that the second elongate body is moved from an open configuration to a closed configuration. In some embodiments, the dilator is inserted within a pelvic region prior to placing a portion of the implant through the opening defined by the proximal end portion of the dilator. In some embodiments, the method includes inserting the dilator within a pelvic region after placing a portion of the implant through the opening defined by the proximal end portion of the dilator. In some embodiments, the method includes, drawing the dilator through a pelvic tissue such that a portion of the implant is disposed within the pelvic tissue. In some embodiments, the method includes coupling a distal end portion of the dilator to a delivery device and inserting the delivery device into a pelvic region.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents.

The previous description of the embodiments is provided to enable a person skilled in the art to make and/or use the invention. While the invention has been particularly shown and described with reference to embodiments thereof, it will be understood by those skilled in art that various changes in form and details may be made therein without departing from the spirit and scope of the invention.

For example, the dilator devices described herein (e.g., 130, 230, 330, etc.) can include various combinations and/or sub-combinations of the components and/or features of the different embodiments described. For example, the connection at the distal end of the dilator devices to associate the dilator to a delivery device can be configured for use with either of the delivery devices described herein, or other delivery devices not specifically described. The dilator devices and delivery devices described herein can also be used to deliver and secure pelvic implants not specifically described herein, such as implants having anchors and or sutures.

An implant according to any of the embodiments can be assembled to a dilator device by a user (e.g., physician) or provided preassembled to the user. The implants and dilator devices can also be delivered using other delivery devices not described herein. The implants described herein are merely examples, as other types of pelvic implants can be coupled to a dilator device as described herein for delivery into a pelvic region of a patient. An implant according to the invention can have a variety of different shapes and sizes, such as for example, circular, square, rectangular, elliptical, oval, diamond shaped, triangular, and can include features such as arms and/or straps.

What is claimed is:

1. An apparatus, comprising: an elongate body, having a proximal end portion and a distal end portion, the elongate body being tapered such that the proximal end portion has a diameter greater than a diameter of the distal end portion, the distal end portion of the elongate body configured to releasably couple the elongate body to a delivery device, the elongate body defining a lumen extending through the proximal end portion and the distal end portion; a lock tube including an elongated member having a tubular structure, the lock tube being movable disposable within the lumen of the elongate body such that at least a portion of the lock tube extends outside the lumen from the proximal end portion of the elongate body; a connector disposed at the proximal end portion of the elongate body, the connector configured to releasable couple a pelvic implant to the elongate body, the lock tube configured to be slidable moved to a position adjacent the pelvic implant to secure the pelvic implant to the elongate body, the connector including a suture, the suture forming a loop portion configured to releasably couple the pelvic implant; and a stop member movable disposed directly on the loop portion of the suture, the stop member being configured to limit the travel of the lock tube relative to the elongate body.

2. The apparatus of claim 1, further comprising:
a trocar coupled to the distal end portion of the elongate body and configured to releasably couple the elongate body to the delivery device.

3. The apparatus of claim 1, further comprising:
a flange disposed within the lumen of the elongate body configured to limit the travel of the lock tube relative to the elongate body.

4. The apparatus of claim 1, further comprising:
a connector at the distal end portion of the elongate body configured to releasably couple the elongate body to a delivery device.

5. The apparatus of claim 1, wherein the lock tube includes a tapered portion extending from a proximal end portion of the elongated member of the lock tube, the lock tube including a cup portion extending from the tapered portion, the cup portion having a diameter greater than a diameter of the elongate body, the cup portion defining a cavity such that a portion of the pelvic implant is disposed within the cavity of the cup portion when the lock tube is proximally moved in relation to the elongate body.

6. A method, comprising:
placing a portion of an implant through an opening defined by a loop portion of a dilator, the dilator including a proximal end portion and a distal end portion, the loop portion extending from the proximal end portion;
moving a stop member of the dilator along the loop portion of the dilator in a first direction, the stop member of the dilator being movably disposed directly on the loop portion, the stop member tightening the loop around the portion of the implant by moving the stop member towards the proximal end portion of the dilator, the stop member engaging a first edge portion of the implant; and
moving a first elongate body of the dilator relative to a second elongate body of the dilator in a second direction opposite to the first direction to engage a second edge portion of the implant, the portion of the implant being secured between the stop member and the first elongate body of the dilator.

7. The method of claim 6, wherein the loop portion includes a suture loop, the opening is defined by a suture coupled to the second elongate body, and the moving includes slidable moving the first elongate body within a lumen defined by the second elongate body to a portion adjacent the implant.

8. The method of claim 6, further comprising:
inserting the dilator within a pelvic region prior to the placing.

9. The method of claim 6, further comprising:
inserting the dilator within a pelvic region after the placing.

10. The method of claim 6, further comprising:
drawing the dilator through a pelvic tissue such that a portion of the implant is disposed within the pelvic tissue.

11. The method of claim 6, further comprising:
coupling the distal end portion of the dilator to a delivery device; and
inserting the delivery device into a pelvic region.

12. An apparatus, comprising:
an elongate body having a proximal end portion and a distal end portion, the elongate body being tapered such that the proximal end portion has a diameter greater than a diameter of the distal end portion the distal end portion of the elongate body configured to releasably couple the elongate body to a delivery device, the elongate body defining a lumen extending through the proximal end portion and the distal end portion;

a lock tube including an elongated member having a tubular structure, the lock tube being movable within the lumen of the elongate body such that at least a portion of the lock tube extends outside the lumen from the proximal end portion of the elongate body;

a connector including a suture, the suture including a first portion disposed through the lumen of the elongate body, a second portion forming a loop portion extending from the proximal end portion of the elongate body, and a third portion extending from the distal end portion of the elongate body, the loop portion configured to releasable couple a pelvic implant to the elongate body, the lock tube configured to be slidably moved along the loop portion of the suture to a position adjacent to the pelvic implant to secure the pelvic implant to the elongate body; and a stop member movable disposed on the loop portion of the suture and configured to limit the travel of the lock tube relative to the elongate body, the stop member being configured to tighten the loop portion around the pelvic implant by moving the stop member towards the proximal end portion of the elongate body.

13. The apparatus of claim 12, further comprising:
a trocar coupled to the third portion of the suture and configured to releasably couple the elongate body to the delivery device.

14. The apparatus of claim 12, wherein the lock tube includes a tapered portion extending from a proximal end portion of the elongated member of the lock tube, the lock tube including a cup portion extending from the tapered portion, the cup portion having a diameter greater than a diameter of the elongated member of the lock tube, the cup portion having a diameter greater than a diameter of the elongate body, the cup portion defining a cavity such that a portion of the pelvic implant is disposed with the cavity of the cup portion when the lock tube is proximally moved along the loop portion of the suture.

* * * * *